United States Patent
Ohmizu et al.

(10) Patent No.: US 6,248,743 B1
(45) Date of Patent: *Jun. 19, 2001

(54) BUTADIENE DERIVATIVES AND PROCESS FOR PREPARING THEREOF

(75) Inventors: Hiroshi Ohmizu, Kyoto; Akio Ohtani, Kawaguchi; Tsuyoshi Ohgiku, Nishinomiya; Hiroshi Sai, Sanda; Jun Murakami, Omiya, all of (JP)

(73) Assignee: Tanabe Seiyaku Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/143,358

(22) Filed: Aug. 28, 1998

Related U.S. Application Data

(63) Continuation of application No. PCT/JP97/01017, filed on Mar. 26, 1997.

(30) Foreign Application Priority Data

Mar. 29, 1996 (JP) .................................... 8-077866
Feb. 13, 1997 (JP) .................................... 9-028581

(51) Int. Cl.$^7$ ..................... A61K 31/495; A61K 31/44; A61K 31/40; C07D 241/04; C07D 401/00
(52) U.S. Cl. ................... 514/255.01; 514/343; 514/352; 514/425; 544/382; 546/309; 546/278.1; 548/547
(58) Field of Search ............................ 544/382; 514/255, 514/343, 352, 425; 546/309, 278.7; 548/547

(56) References Cited

U.S. PATENT DOCUMENTS

| | | | |
|---|---|---|---|
| 4,343,796 | 8/1982 | Groen | 424/184 |
| 5,639,789 | * 6/1997 | Iwasaki et al. | 514/539 |

FOREIGN PATENT DOCUMENTS

| | | |
|---|---|---|
| 0 420 397 | 4/1991 | (EP) . |
| 0 563 798 | 10/1993 | (EP) . |

OTHER PUBLICATIONS

Sakakibara, I. et al. Phytochemistry. vol. 38, No. 4, pp 1003–1007 (1995).*
Nishiyama, A. et al. Chem. Pharm. Bull. vol. 31, No. 8, pp2845–2852 (1983).*

Chemical Abstracts, vol. 112, No. 1, Abstract No. 7309x, p. 717, Jan. 1, 1990, "Heterocyclic fulgides based on 1,2–dimethyl–3–=formylindole," G.I Yu et al.

Heterocycles, vol. 27, No. 9, 1988, pp. 2185–2195, New Synthetic Route to Butanolide Lignans by a Ruthenium Complex Catalyzed Hydrogenation of the Corresponding Stobbe's Fulgenic Acids by Massimo Bambagiotti–Alberti et al.

Nouveau Journal de Chemie, vol. 1, No. 2, 1977, pp. 413–418, "Cathodic Reduction of Derivatives of Dibenzylidenesuccinic Acid; Attempted Electro–Hydrocyclization of Conjugated Systems" by J. Andersson et al.

* cited by examiner

*Primary Examiner*—Deborah C. Lambkin
(74) *Attorney, Agent, or Firm*—Finnegan, Henderson, Farabow, Garrett & Dunner, L.L.P.

(57) ABSTRACT

A novel butadiene derivative of the formula:

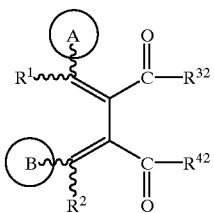

(1-a)

wherein Ring A is heterocycle, or benzene being optionally substituted by lower alkyl, alkoxy, nitro, hydroxy, substituted or unsubstituted amino or halogen, Ring B is heterocycle, or benzene being optionally substituted by lower alkoxy, lower alkylenedioxy or di-lower alkylamino, $R^1$ and $R^2$ are each H or lower alkyl, one of —$COR^{32}$ and —$COR^{42}$ is carboxyl, and the other is carboxyl being optionally esterified, or the corresponding amide or pyrrolidine derivatives, or a pharmaceutically acceptable salt thereof. Said compounds show excellent PAI-1 inhibitory activity and are useful in the prophylaxis or treatment of various thromboses such as myocardial infarction, intraatrial thrombus in atrial fibrillation, cerebral infarction, angina pectoris, stroke, pulmonary infarction, deep venous thrombus (DVT), disseminated intravascular coagulation syndrome (DIC), diabetic complications, restenosis after percutaneous transluminal coronary angioplasty (PTCA), etc.

20 Claims, No Drawings

BUTADIENE DERIVATIVES AND PROCESS FOR PREPARING THEREOF

This application is a continuation application of PCT international application No. PCT/JP97/01017 which has an international filing date of Mar. 26, 1997 which designated the United States, the entire contents of which are incorporated by reference.

TECHNICAL FIELD

The present invention relates to a novel butadiene derivative and a novel pyrrolidine derivative, both having excellent activity for inhibiting the activity or production of type 1 plasminogen activator inhibitor (PAI-1) in living body and being useful as an antithrombotic agent, and processes for preparing the same.

BACKGROUND ART

Thrombus means the blood coagulation condition in the heart and the blood vessels of the living body, and by which the blood vessels are narrowed or occluded, and then, the circulation disorder is led in the tissues being dominated by said blood vessel, and the onset of necrosis or edema occurs in these tissues. As a result, various arterial and thrombotic diseases are caused such as myocardial infarction, intra-atrial thrombus in atrial fibrillation, arterial sclerosis, angina pectoris, stroke, pulmonary infarction, deep venous thrombus (DVT), disseminated intravascular coagulation syndrome (DIC), diabetic complications, restenosis after percutanous transluminal coronary angioplasty (PTCA), etc.

Various factors are considered to participate in the formation of thrombus, for example, the change in the conditions of the blood vessel wall, the change in the blood flow speed, and the change in the components of the plasma. The components of thrombus are, for example, platelets, erythrocytes, leukocytes, fibrin, etc.

In many cases, the fibrinolysis (fibrinolytic system) is secondarily activated in the living body in order to lyse microthrombus being formed in the living body. For instance, plasminogen, inactive precursor, is converted into active plasmin (a protease existing mainly in the plasma) by a plasminogen activator being specific to the active site thereof (PA; tissue plasminogen activator (t-PA), urokinase plasminogen activator (u-PA), etc.), and activated plasmin can interrupt the lysine-bond of polypeptide chain of fibrin, by which thrombus is lysed. On the other hand, the activity of PA is controlled by its specific inhibitor, Type 1 plasminogen activator inhibitor (PAI-1).

Therefore, the activity of the fibrinolysis is determined by the valance between the amount of PA, and the PAI-1, both secreted from the vascular endothelial cells, and the increase or decrease in the PAI-1 production in cells, or the change in the activity of PAI-1 molecule per se immediately affect the fibrinolysis in the blood.

In another word, it may be possible to prevent or treat various thrombotic diseases represented by the above-mentioned diseases by acting directly on the vascular endothelial cells and inhibiting PAI-1 activity or the production thereof, and by increasing PA activity.

Under the above circumstances, there have widely been used enzyme preparations such as tissue plasminogen activator, urokinase, streptokinase, etc. for lysis and prevention of thrombus. These drugs have, however, some deficits, for example, they are rapidly inactivated in the blood and as a result they lose their pharmacological activities in a very short time, or they can be administered only by parenteral route but not by oral route.

On the other hand, EP-A-563798 discloses as an antithrombotic agent 3-[(E)-benzylidene]-4-[(E)-3,4,5-trimethoxybenzylidene]-2,5-pyrrolidinedione and (E)-2-[(E)-3,4,5-trimethoxybenzylidene]-3-carboxy-4-phenyl-3-butenoic acid methyl ester, but these compounds also have some deficits such as less bio-availability, less safety as a medicament, and stability thereof, for example, (1) low solubility in water, (2) easily metabolized in the liver, (3) toxicity against in the liver and chromosome, etc.

Besides, Nouveau Journal De Chimie, vol. 1, No. 5, p 413–418 (1977) discloses benzylidenesuccinic acid as a product of reduction of electrolytes, but the pharmacological activities thereof have never been disclosed hitherto.

DISCLOSURE INVENTION

An object of the present invention is to provide novel butadiene derivatives and novel pyrrolidine derivatives having no drawback of the above-mentioned conventional antithrombotic agents, which can be administered either orally or parenterally and show an excellent antithrombotic activity. Another object of the present invention is to provide a process for preparing these compounds.

The present inventors have intensively studied and have found a novel butadiene derivative and a novel pyrrolidine derivative showing excellent antithrombotic activities by inhibiting the production of PAI-1, and finally have accomplished the present invention.

That is, the present invention relates to a butadiene derivative of the formula (1-a):

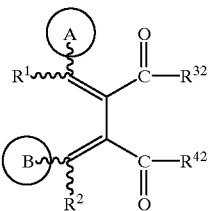

(1-a)

wherein
Ring A is a substituted or unsubstituted heterocyclic group, or a benzene ring which may optionally be substituted by a group selected from a lower alkyl group, an alkoxy group, a nitro group, a hydroxy group, a substituted or unsubstituted amino group and a halogen atom, Ring B is a substituted or unsubstituted heterocyclic group, or a benzene ring which may optionally be substituted by a group selected from a lower alkoxy group, a lower alkylenedioxy group and a di-lower alkylamino group, $R^1$ and $R^2$ are the same or different, and each are a hydrogen atom or a lower alkyl group, one of a group: $-COR^{32}$ and a group: $-COR^{42}$ is a carboxyl group, and the other is a carboxyl group which may optionally be esterified, provided that both Ring A and Ring B are not simultaneously an unsubstituted benzene ring, and when Ring A is a tri-lower alkoxybenzene ring, then Ring B is a substituted or unsubstituted heterocyclic group, or at least one of $R^1$ and $R^2$ is a lower alkyl group, or a pharmaceutically acceptable salt thereof.

The present invention also provides an amidobutadiene derivative of the formula (1-b):

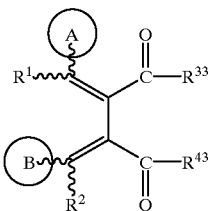

(1-b)

wherein
Ring A is a substituted or unsubstituted heterocyclic group, or a benzene ring which may optionally be substituted by a group selected from a lower alkyl group, an alkoxy group, a nitro group, a hydroxy group, a substituted or unsubstituted amino group and a halogen atom,
Ring B is a substituted or unsubstituted heterocyclic group, or a benzene ring which may optionally be substituted by a group selected from a lower alkoxy group, a lower alkylenedioxy group and a di-lower alkylamino group,
$R^1$ and $R^2$ are the same or different, and each are a hydrogen atom or a lower alkyl group,
one of a group: —$COR^{33}$ and a group: —$COR^{43}$ is an amidated carboxyl group, and the other is a carboxyl group which may optionally be esterified, or an amidated carboxyl group,
provided that both Ring A and Ring B are not simultaneously an unsubstituted benzene ring, and when Ring A is a tri-lower alkoxybenzene ring, then Ring B is a substituted or unsubstituted heterocyclic group, or at least one of $R^1$ and $R^2$ is a lower alkyl group, or a pharmaceutically acceptable salt thereof.

The present invention further provides a pyrrolidine derivative of the formula (2):

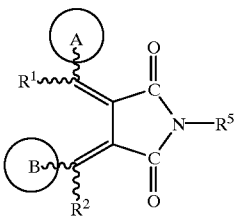

(2)

wherein
Ring A is a substituted or unsubstituted heterocyclic group, or a benzene ring which may optionally be substituted by a group selected from a lower alkyl group, an alkoxy group, a nitro group, a hydroxy group, a substituted or unsubstituted amino group and a halogen atom,
Ring B is a substituted or unsubstituted heterocyclic group, or a benzene ring which may optionally be substituted by a group selected from a lower alkoxy group, a lower alkylenedioxy group and a di-lower alkylamino group,
$R^1$ and $R^2$ are the same or different, and each are a hydrogen atom or a lower alkyl group, $R^5$ is a hydrogen atom, a substituted or unsubstituted alkyl group, a substituted or unsubstituted amino group, or a substituted or unsubstituted nitrogen-containing heterocyclic group,
provided that both Ring A and Ring B are not simultaneously an unsubstituted benzene ring, and when Ring A is a tri-lower alkoxybenzene ring, then Ring B is a substituted or unsubstituted heterocyclic group, or at least one of $R^1$ and $R^2$ is a lower alkyl group, or a pharmaceutically acceptable salt thereof.

The heterocyclic group for Ring A and Ring B of the butadiene derivative (1-a), the amidobutadiene derivative (1-b) and the pyrrolidine derivative (2) includes, for example, a 5- or 6-membered nitrogen-containing heteromonocyclic group such as pyridine ring, pyrimidine ring, etc. Besides, said heterocyclic group may optionally have a substituent, such as an oxo group, a hydroxy group, a lower alkoxy group, a halogen atom, etc.

Among the substituents on the benzene ring for Ring A, the lower alkyl group is methyl, ethyl, propyl, butyl, etc., and the alkoxy group is a lower alkoxy group (e.g. methoxy, ethoxy, butoxy, etc.), a lower alkylenedioxy group (e.g. methylenedioxy, etc.), a cycloalkyloxy group (e.g. cyclopropyloxy, cyclopentyloxy, cyclohexyloxy, etc.), and methoxy and cyclopentyloxy are preferable. The substituted or unsubstituted amino group includes a di-lower alkylamino group such as dimethylamino, diethylamino, etc., and the halogen atom is fluorine, chlorine, bromine, iodine, etc., and chlorine is preferable.

The lower alkoxy group on the benzene ring for Ring B is methoxy, ethoxy, propyloxy, butoxy, etc., and methoxy is preferable. The lower alkylenedioxy group on the benzene ring for Ring B is methylenedioxy, ethylenedioxy, etc., and the di-lower alkylamino group is dimethylamino, diethyl amino, etc.

The lower alkyl group for $R^1$ or $R^2$ is methyl, ethyl, propyl, isopropyl, butyl, etc., and methyl is preferable.

When a group: —$COR^{32}$, a group: —$COR^{42}$, a group: —$COR^{33}$ or a group: —$COR^{43}$ is an esterified carboxyl group, said ester residue includes, for example, a lower alkyl group (e.g. methyl, ethyl, isopropyl, propyl, butyl, etc.), a lower alkoxy-substituted lower alkyl group (e.g. methoxymethyl, 2-methoxyethyl, etc.), and methyl, isopropyl and 2-methoxyethyl are preferable, especially methyl is most preferable. When a group: —$COR^{33}$ or a group: —$COR^{43}$ is an amidated carboxyl group, such group includes, for example, a carbamoyl group which may optionally be substituted by one or two groups selected from a substituted or unsubstituted alkyl group, a substituted or unsubstituted phenyl group, a substituted or unsubstituted amino group and a substituted or unsubstituted nitrogen-containing heterocyclic group, or a group of the formula:

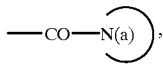

wherein Ring (a) is a substituted or unsubstituted 5- or 6-membered nitrogen-containing heteromonocyclic group.

The substituted or unsubstituted alkyl group, for a group: —$COR^{33}$, a group: —$COR^{43}$ and $R^5$ includes, for example, a lower alkyl group (e.g. methyl, ethyl, isopropyl, butyl, etc.), a pyridyl- or 1-oxopyridyl-lower alkyl group (e.g. pyridylmethyl, pyridylethyl, 1-oxopyridylmethyl, etc.), a piperazinyl-lower alkyl group (e.g. piperazinylmethyl, etc.), a piperidyl-lower alkyl group (e.g. piperidylmethyl, etc.), a hydroxy-lower alkyl group (e.g. hydroxyethyl, etc.), a di-lower alkylamino-lower alkyl group (e.g. dimethylaminoethyl, diethylaminomethyl, diethylaminoethyl, etc.), etc., and the substituted or unsubstituted phenyl group includes, for example, phenyl, a di-lower alkylaminophenyl group (e.g. dimethylaminophenyl, etc.), a morpholinophenyl group, a lower alkylpiperazinylcarbonylphenyl group (e.g. methylpiperazinylcarbonylphenyl, etc.), etc. The substituted or unsubstituted amino group includes, for example, an amino group, a di-lower alkylamino group (e.g. dimethylamino, diethylamino, etc.), a morpholino-lower alkylamino group (e.g. morpholinomethylamino, etc.), and the substituted or unsubstituted nitrogen-containing heterocyclic group includes, for example, a 5- or 6-membered nitrogen-containing heteromonocyclic group such as a pyridine ring which may optionally be substituted by an amino group, a lower alkoxy group or an oxo group, a piperazine ring which may optionally be substituted by a group selected from an oxo group and a lower alkyl group, a piperidine ring which may optionally be substituted by a lower alkyl group, an isoxazole ring which may optionally be substituted by a lower alkyl group, a pyrazole ring, a triazole ring, or a pyrimidine ring.

The nitrogen-containing heteromonocyclic group of Ring (a) includes a 5- or 6-membered nitrogen-containing heteromonocyclic group such as a piperazinyl group, a piperidyl group, a morpholinyl group, a pyrazolyl group, these groups being optionally substituted by a lower alkyl group or an amino group, etc.

The preferable compounds (1-a) are compounds of the formula (1-a) wherein a group: —$COR^{32}$ is an esterified carboxyl group and a group: —$COR^{42}$ is a carboxyl group. The preferable compounds (1-b) are compounds of the formula (1-b) wherein a group: —$COR^{33}$ is an esterified carboxyl group and a group: —$COR^{43}$ is an amidated carboxyl group.

Other preferably compounds (1-a), (1-b) and (2) are compounds of these formulae wherein Ring A is a benzene ring substituted by a group selected from an alkoxy group, a nitro group, a hydroxy group, a di-lower alkylamino group and a halogen atom, Ring B is a 5- or 6-membered nitrogen-containing heteromonocyclic group, a benzene ring, or a lower alkylenedioxy-substituted benzene ring, and the more preferable compounds are compounds of these formulae wherein Ring A is a benzene ring substituted by two or three groups selected from a lower alkoxy group, a nitro group, a hydroxy group, a di-lower alkylamino group and a halogen atom, Ring B is a pyridine ring, a benzene ring or a lower alkylenedioxy-substituted benzene ring, $R^1$ is a lower alkyl group, and $R^2$ is a hydrogen atom.

Further preferable compounds (1-b) are compounds of the formula (1-b) wherein a group: —$COR^{33}$ is a lower alkoxycarbonyl group or a lower alkoxy-substituted lower alkoxycarbonyl group, a group: —$COR^{43}$ is a carbamoyl group substituted by one group selected from a pyridyl group, an oxo-substituted pyridyl group, an amino-substituted pyridyl group, a lower alkoxy-substituted pyridyl group, a lower alkyl-substituted piperidyl group, a lower alkyl-substituted piperazinyl group, a piperazinyl group substituted by a lower alkyl group and an oxo group, a lower alkyl-substituted isoxazolyl group, a pyrazolyl group, a triazolyl group, a pyridyl-substituted lower alkyl group, an oxo-substituted pyridyl-lower alkyl group, a di-lower alkylphenyl group, a morpholinophenyl group, a lower alkylpiperazinylcarbonylphenyl group, a hydroxy-lower alkyl group and a di-lower alkylamino group, or a group of the formula:

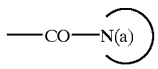

wherein Ring (a) is a substituted or unsubstituted 5- or 6-membered nitrogen-containing heteromonocyclic group.

Further preferably compounds (2) are compounds of the formula (2) wherein $R^5$ is a pyridyl-substituted lower alkyl group, a di-lower alkylamino-lower alkyl group, a hydroxy-lower alkyl group, a di-lower alkylamino group, or a lower alkyl-substituted piperazinyl group.

The more preferable compounds (1-a), (1-b) and (2) are compounds of the formulae (1-a), (1-b) and (2) wherein Ring A is a benzene ring substituted by two or three groups selected from a methoxy group, a cyclopentyloxy group, a nitro group, a hydroxy group, a dimethylamino group and a chlorine atom, and $R^1$ is a methyl group.

The most preferable compounds (1-b) are compounds of the formula (1-b) wherein a group: —$COR^{33}$ is a methoxycarbonyl group, an isopropyloxycarbonyl group or a 2-methoxyethoxycarbonyl group, a group: —$COR^{43}$ is an unsubstituted carbamoyl group or a carbamoyl group substituted by one group selected from a pyridylmethyl group, a 2-aminopyridyl group, a pyridyl group, a 1-oxopyridyl group, a 4-methylpiperazinyl group, a 4-methyl-4-oxopiperazinyl group, a 1-methylpiperidyl group, a 5-methylisoxazolyl group, a 3-pyrazolyl group, a 1,3,4-triazolyl group, a 1-oxopyridylmethyl group, a dimethylaminoethyl group, a hydroxyethyl group and a dimethylamino group. The most preferable compounds (2) are compounds of the formula (2) wherein $R^5$ is a hydrogen atom, a pyridylmethyl group, a dimethylaminoethyl group, a hydroxyethyl group, a dimethylamino group, or a 4-methylpiperazinyl group.

The desired compounds (1-a), (1-b) and (2) of the present invention have four stereoisomers based on two double bonds thereof, respectively, and also have optical isomers based on an asymmetric carbon atom thereof, but the present invention also includes these isomers and a mixture thereof as well.

Among these four stereoisomers, preferable isomers are ones having a trans(E)-configuration based on the double bond binding to Ring B, and among these isomers, more preferable isomers are ones having a cis(Z)-configuration based on the double bond binding to Ring A.

Among the desired compounds of the present invention, preferable compounds are the compounds (1-b) and (2), and among these compounds, more preferable compounds are the compounds (1-b).

Preferable compounds (1-b) of the present invention are (1Z,3E)-1-methyl-1-(3,5-dimethoxyphenyl)-2-methoxycarbonyl-3-[N-(4-methylpiperazin-1-yl)aminocarbonyl]-4-phenylbutadiene;

(1Z,3E)-1-methyl-1-(3,5-dimethoxyphenyl)-2-methoxycarbonyl-3-[N-(4-pyridyl)aminocarbonyl]-4-(3,4-methylenedioxyphenyl)butadiene;

(1Z,3E)-1-methyl-1-(3,5-dimethoxyphenyl)-2-methoxycarbonyl-3-[N-(4-pyridylmethyl)aminocarbonyl]-4-phenylbutadiene;

(1Z,3E)-1-methyl-1-(3-chloro-4,5-dimethoxyphenyl)-2-methoxycarbonyl-3-[N-(3-pyridylmethyl)aminocarbonyl]-4-phenylbutadiene, and (1Z,3E)-1-methyl-1-(3-chloro-4,5-dimethoxyphenyl)-2-methoxycarbonyl-3-aminocarbonyl-4-(4-pyridyl)butadiene, or a pharmaceutically acceptable salt thereof, etc.

Preferable compounds (2) of the present invention are (3Z,4E)-3-(3,5-dimethoxy-α-methylbenzylidene)-4-benzylidene-1-(4-pyridylmethyl)pyrrolidine-2,5-dione; (3Z,4E)-3-(3-chloro-4,5-dimethoxy-α-methylbenzylidene)-4-(4-pyridylmethylidene)pyrrolidine-2,5-dione; (3Z,4E)-3-(3-methoxy-4-cyclopentyloxy-α-methylbenzylidene)-4-(4-pyridylmethylidene)pyrrolidine-2,5-dione; (3Z,4E)-3-(3-cyclopentyloxy-4-methoxy-α-methylbenzylidene)-4-(4-pyridylmethylidene)pyrrolidine-2,5-dione, and (3Z,4E)-3-(3,5-dimethoxy-α-methylbenzylidene)-4-(4-pyridylmethylidene)pyrrolidine-2,5-dione, or a pharmaceutically acceptable salt thereof, etc.

The desired compounds (1-a), (1-b) and (2) of the present invention may be used in clinical use either in the free from or in the form of a pharmaceutically acceptable salt thereof. The pharmaceutically acceptable salt includes, for example, salts with an inorganic acid (e.g. hydrochloride, sulfate, hydrobromide, etc.), salts with an organic acid (e.g. acetate, fumarate, oxalate, methane-sulfonate, etc.). When the desired compounds of the present invention have a substituent such as a carboxyl group, an imide group, etc., these compounds may be used in the form of a basic salt thereof such as an alkali metal salt (e.g. sodium salt, potassium salt, etc.) or an alkaline earth metal salt (e.g. calcium salt, etc.). The compounds of the present invention and a pharmaceutically acceptable salt thereof also include hydrates and solvates thereof.

The desired compounds (1-a), (1-b) and (2) of the present invention and a pharmaceutically acceptable salt thereof may be administered either orally or parenterally, and administered in the form of a pharmaceutical preparation such as tablets, granules, capsules, powders, injections, inhalants, etc.

The dosage of the desired compounds (1-a), (1-b) and (2) of the present invention and a pharmaceutically acceptable salt thereof may vary depending on the administration route, the ages, weights and conditions of the patients, or severity of diseases to be cured, but it is usually in the range of about 0.1 to 100 mg/kg/day in the case of oral administration. In the case of parenteral administration, it is in the range of about 0.01 to 10 mg/kg/day.

The desired compound (1-a) of the present invention may be prepared by treating a diester compound of the formula (4):

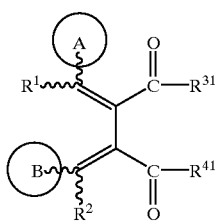

(4)

wherein a group: —COR$^{31}$ and a group: —COR$^{41}$ are the same or different and each are an esterified carboxyl group, and Ring A, Ring B, R$^1$ and R$^2$ are the same as defined above, with an acid or a base.

The desired compound (1-b) of the present invention may be prepared by reacting a compound (1-a), or a salt thereof, or a reactive derivative thereof, with a compound of the formula (5):

H—R$^{40}$ (5)

wherein R$^{40}$ is a substituted or unsubstituted amino group.

The desired compound (2) of the present invention may be prepared by subjecting a compound of the formula (1-c):

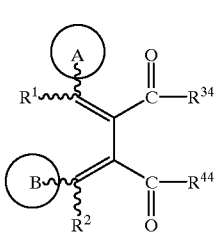

(1-c)

wherein one of a group: —COR$^{34}$ and a group: —COR$^{44}$ is a carboxyl group which may optionally be esterified, and the other is a carbamoyl group, a substituted or unsubstituted alkyl group-substituted carbamoyl group, a substituted or unsubstituted amino-substituted carbamoyl group, or a substituted or unsubstituted nitrogen-containing heterocyclic group-substituted carbamoyl group, and Ring A, Ring B, R$^1$ and R$^2$ are the same as defined above, or a salt thereof, to intramolecular cyclization reaction.

The desired compound (2) wherein R$^5$ is a substituted or unsubstituted alkyl group, a substituted or unsubstituted amino group, or a substituted or unsubstituted nitrogen-containing heterocyclic group may be prepared by reacting a compound of the formula (2-a):

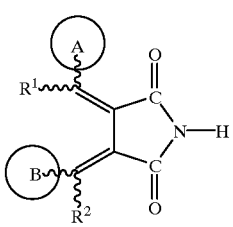

(2-a)

wherein Ring A, Ring B, R$^1$ and R$^2$ are the same as defined above, or a salt thereof, with a compound of the formula (3):

R$^{51}$—X (3)

wherein R$^{51}$ is a substituted or unsubstituted alkyl group, a substituted or unsubstituted amino group, or a substituted or unsubstituted nitrogen-containing heterocyclic group, and X is a reactive residue.

The treatment of the diester compound (4) with an acid or a base is carried out in a suitable solvent or without a solvent.

The solvent may be any inert solvent which does not disturb the reaction, for example, organic solvents such as ethylene glycol, N,N-dimethylformamide, hexamethylphosphoramide, benzene, tetrahydrofuran, dioxane, toluene, ethyl acetate, a lower alcohol (methanol, ethanol, etc.), dichloromethane, 1,2-dichloroethane, chloroform, carbon tetrachloride, 1,3-dimethyl-2-imidazolidinone, diethyl ether, dimethoxyethane, dimethyl sulfoxide, carbon disulfide, acetone, etc., or a mixture of these solvents and water.

The base includes, for example, an alkali metal, an alkali metal hydroxide, an alkali metal hydride, an alkali metal alkoxide, an alkali metal alkyl amide (e.g. lithium diisopropyl amide (LDA). etc.), a lower alkyl alkali metal (e.g. n-butyl lithium, etc.), or an organic amine such as a tri-lower alkylamine, 1,8-diazabicyclo[5.4.0]undeca-7-ene, etc. The acid includes either a conventional protonic acid or a conventional Lewis acid.

The reaction is preferably carried out under cooling or with heating, for example, at a temperature between −60° C. and 150° C., preferably at a temperature between 15° C. and a boiling point of the solvent to be used.

The condensation reaction between the compound (1-a) or a salt thereof and the compound (5) is carried out in the presence of a dehydrating agent in a suitable solvent.

The dehydrating agent includes, for example, 1,3-dicyclohexylcarbodiimide (DCC), carbonyl diimidazole (CDI), etc.

The salt of the compound (1-a) may be a conventional salt such as a salt with an alkali metal or alkaline earth metal, etc. These salts may preferably be converted in advance into a free compound and then used in the reaction with the compound (5).

The condensation reaction between a reactive derivative of the compound (1-a) and the compound (5) is carried out in the presence of an acid acceptor in a suitable solvent.

The reactive derivative may be any conventional ones which are suitable for the acid-amide bond producing reaction, for example, acid halides, mixed acid anhydrides, active esters, etc.

The acid acceptor includes, for example, alkali metal hydroxides, alkali metal carbonates, alkali metal hydrogen carbonates, trialkylamines, N,N-dialkylanilines, pyridine, etc.

The solvent includes, for example, dichloromethane, chloroform, 1,2-dichloroethane, diethyl ether, tetrahydrofuran, dioxane, N,N-dimethylformamide, dimethyl sulfoxide, toluene, benzene, etc.

The compound (5) is used in an amount of 1 to 3 moles, preferably in an amount of 1.1 to 1.3 mole, to 1 mole of the compound (1-a), a salt thereof, or a reactive derivative thereof.

The intramolecular cyclization reaction of the compound (1-c) is preferably carried out in the presence of a base or an acid in a suitable solvent or without a solvent.

The solvent may be any inert solvent which does not disturb the reaction, for example, organic solvents such as ethylene glycol, N,N-dimethylformamide, hexamethylphosphoramide, benzene, tetrahydrofuran, dioxane, toluene, ethyl acetate, a lower alcohol (e.g. methanol, ethanol, etc.), dichloromethane, 1,2-dichloroethane, chloroform, carbon tetrachloride, 1,3-dimethyl-2-imidazolidinone, diethyl ether, dimethoxyethane, dimethyl sulfoxide, carbon disulfide, acetone, etc., or a mixture of these organic solvents and water.

The base includes, for example, an alkali metal, an alkali metal hydroxide, an alkali metal hydride, an alkali metal alkoxide, an alkali metal alkyl amide (e.g. lithium diisopropyl amide (LDA). etc.), a lower alkyl alkali metal (e.g. n-butyl lithium, etc.), or an organic amine such as a tri-lower alkylamine, 1,8-diazabicyclo[5.4.0]undeca-7-ene, etc. The acid includes a conventional protonic acid or a conventional Lewis acid.

The reaction is carried out under cooling or with heating, for example, at a temperature between −60° C. and 150° C., preferably at a temperature between 15° C. and a boiling point of the solvent to be used.

The condensation reaction between the compound (2-a) or a salt thereof and the compound (3) is carried out in the presence of an acid acceptor in a suitable solvent.

The salt of the compound (2-a) is, for example, an alkali metal salt, etc.

The acid acceptor may be any conventional ones, and includes, for example, alkali metal hydrides (e.g. sodium hydride), alkali metal hydroxides (e.g. sodium hydroxide), alkali metal carbonates (e.g. potassium carbonate), alkali metal alkoxides (e.g. sodium methoxide), alkali metal alkyl amides (e.g. lithium diisopropylamide), or alkali metals (e.g. sodium).

The reactive residue X includes, for example, a halogen atom (e.g. chlorine, bromine, iodine, etc.), a sulfonyloxy group (e.g. trifluoromethanesulfonyloxy, toluenesulfonyloxy, methanesulfonyloxy, etc.), etc.

The solvent includes, for example, dichloromethane, chloroform, 1,2-dichloroethane, diethyl ether, tetrahydrofuran, dioxane, ethylene glycol, N,N-dimethylformamide, dimethyl sulfoxide, toluene, benzene, etc.

The condensation reaction is carried out under cooling or with heating, for example, a temperature between −60° C. and 100° C., preferably at a temperature between −60° C. and 20° C.

The compound (3) is used in this reaction in an amount of 1 to 5 moles, to 1 mole of the compound (2-a) or a salt thereof.

The starting compound (4) may be prepared by reacting a compound of the formula (6):

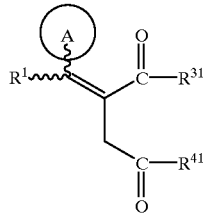

(6)

wherein Ring A, $R^1$, —$COR^{31}$ and —$COR^{41}$ are the same as defined above, with a compound of the formula (7):

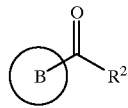

(7)

wherein Ring B and $R^2$ are the same as defined above.

The starting compound (4) may also be prepared by reacting a compound of the formula (8):

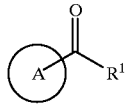

(8)

wherein Ring A and $R^1$ are the same as defined above, with a compound of the formula (9):

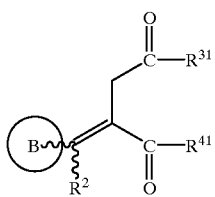

(9)

wherein Ring B, R², —COR³¹ and —COR⁴¹ are the same as defined above.

The condensation reaction between the compound (6) and the compound (7), or the compound (8) and the compound (9) is carried out in the presence of a base in a suitable solvent. The base includes an alkali metal alkoxide or an alkali metal alkyl amide such as potassium tert-butoxide, sodium methoxide, lithium diisopropylamide (LDA), etc. The solvent includes, for example, a lower alcohol (e.g. methanol, ethanol, tert-butyl alcohol, etc.), dichloromethane, chloroform, 1,2-dichloroethane, diethyl ether, tetrahydrofuran, dioxane, ethylene glycol, N,N-dimethylformamide, dimethyl sulfoxide, toluene, benzene, etc.

The reaction is carried out under cooling or with heating, for example, at a temperature between −30° C. and a boiling point of the solvent to be used, more preferably at a temperature between 15° C. and 80° C.

Among the starting compounds (6), a trans(E)-isomer thereof may be prepared, for example, by condensing the compound (8) with a compound of the formula (10):

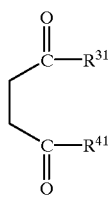

(10)

wherein —COR³¹ and —COR⁴¹ are the same as defined above, in the presence of a base in a suitable solvent.

Among the starting compounds (6), a cis(Z)-isomer thereof may be prepared by addition and elimination reaction of the corresponding trans(E)-isomer, for example, by adding a nucleophilic reagent (e.g. thiophenol) to the trans (E)-isomer of the compound (6), followed by elimination of the nucleophile from the resulting adduct in the presence of a base.

Throughout the present specification and claims, the alkyl group and the alkoxy group mean ones having 1 to 20 carbon atoms, preferably ones having 1 to 10 carbon atoms, more preferably ones having 1 to 6 carbon atoms, respectively. The lower alkyl group and the lower alkoxy group mean ones having 1 to 6 carbon atoms, preferably ones having 1 to 4 carbon atoms, respectively. The cycloalkyl group means ones having 3 to 10 carbon atoms, preferably ones having 5 to 8 carbon atoms. The lower alkylenedioxy group means ones having 1 to 4 carbon atoms.

BEST MODE FOR CARRYING OUT THE INVENTION

The present invention is illustrated in more detail by the following Examples, but should not be construed to be limited thereto.

EXAMPLE 1

(1) To a solution of vanillin (50 g) in N,N-dimethylformamide (600 ml) are added 62.5% sodium hydride (13.9 g) and cyclopentyl bromide (38.8 ml) under ice-cooling, and the mixture is stirred at 90° C. overnight. The mixture is concentrated under reduced pressure to remove the N,N-dimethylformamide, and to the residue is added water. The mixture is extracted with ethyl acetate, and the extract is washed, dried, and concentrated under reduced pressure to remove the solvent. The resulting residue is purified by silica gel column chromatography (eluent; hexane:ethyl acetate=3:1) to give 4-cyclopentyloxy-3-methoxybenzaldehyde (65 g).

Yield: 90%

IR: 2960, 1683, 1583, 1506, 1266, 1135, 730 cm$^{-1}$ (2) A solution of the above product (10 g) and dimethyl succinate (8.0 g) in tert-butyl alcohol (20 ml) is added to a solution of potassium tert-butoxide (5.1 g) in tert-butyl alcohol (50 ml), and the mixture is stirred at room temperature for one hour. The reaction mixture is poured into ice-water, and the mixture is washed with diisopropyl ether. The pH value of the mixture is adjusted to pH 1 with hydrochloric acid, and the mixture is extracted with ethyl acetate. The extract is washed, dried, and concentrated under reduced pressure. The resulting residue is dissolved in dichloromethane (100 ml), and thereto are added diisopropyl ethylamine (11.8 ml) and methoxymethyl chloride (3.9 ml) under ice-cooling, and the mixture is stirred at room temperature for one hour. To the mixture is added water, and the mixture is extracted with ethyl acetate. The extract is washed, dried, and concentrated under reduced pressure. The resulting residue is purified by silica gel column chromatography (eluent; hexane:ethyl acetate=3:1) to give methyl (E)-3-(4-cyclopentyloxy-3-methoxyphenyl)-2-(methoxymethoxycarbonylmethyl)acrylate (10.9 g).

Yield: 63%

IR: 2957, 1741, 1710, 1599, 1513, 1256, 1145 cm$^{-1}$ (3) To a solution of thiophenol (5.9 ml) in tetrahydrofuran (50 ml) is added a 15% solution of n-butyl lithium in hexane (2.2 ml) at 0° C. under nitrogen atmosphere, and the mixture is stirred at room temperature for 30 minutes. To the mixture is added a solution of the compound obtained in the above (2) (13.4 g) in tetrahydrofuran (100 ml), and the mixture is stirred at room temperature overnight. The mixture is extracted with ethyl acetate, and the extract is washed, dried and concentrated under reduced pressure to remove the solvent. The residue is purified by silica gel column chromatography (eluent; hexane:ethyl acetate=3:1) to give methyl (2R*,3S*)-3-(4-cyclopentyloxy-3-methoxyphenyl)-2-methoxymethoxycarbonylmethyl-3-phenylthiopropionate (14.5 g).

Yield: 84%

IR: 2957, 1736, 1585, 1512, 1265, 1143 cm$^{-1}$ (4) To a solution of the above product (14.5 g) in chloroform (300 ml) is added in portions 3-chloroperbenzoic acid (5.1 g) at 0° C. The mixture is stirred at the same temperature for 30 minutes. To the mixture is added calcium hydroxide (10 g), and the mixture is stirred, filtered, and the filtrate is concentrated under reduced pressure. To the residue is added toluene (300 ml), and the mixture is refluxed for 30 minutes. The mixture is concentrated under reduced pressure, and the resulting residue is purified by silica gel column chromatography (eluent; hexane:ethyl acetate=3:1) to give methyl (Z)-3-(4-cyclopentyloxy-3-methoxyphenyl)-2-(methoxymethoxycarbonylmethyl)-acrylate (9.0 g).

Yield: 67%

IR: 2956, 1744, 1718, 1600, 1511, 1144 cm$^{-1}$ (5) A solution of the above product (10.3 g) in tetrahydrofuran (100 ml) is added dropwise to a solution of lithium diisopropylamide which is prepared from diisopropylamine (4.6 ml) and n-butyl lithium (20 ml) in tetrahydrofuran (60 ml) at −78° C. under nitrogen atmosphere, and the mixture is stirred at the same temperature for 30 minutes. To the mixture is added dropwise a solution of benzaldehyde (3.5 g) in tetrahydrofuran (30 ml) at −100° C., and the mixture is stirred at the same temperature for 20 minutes. To the mixture is added aqueous ammonium chloride solution, and the mixture is extracted with ethyl acetate. The extract is washed, dried, and concentrated under reduced pressure. The residue is dissolved in dichloromethane (50 ml), and thereto are added triethylamine (11 ml) and methanesulfonyl chloride (2.5 ml) at 0° C., and the mixture is stirred at room temperature for one hour. Water is added to the mixture, and the mixture is extracted with ethyl acetate. The extract is washed, dried, and concentrated under reduced pressure. The residue is purified by silica gel column chromatography (eluent; hexane:ethyl acetate=3:1) to give (1Z,3E)-1-(4-cyclopentyloxy-3-methoxyphenyl)-2-methoxycarbonyl-3-methoxymethoxycarbonyl-4-phenylbutadiene (7.3 g).

Yield: 58%

IR: 2957, 1717, 1597, 1509, 1264, 1160, 696 cm$^{-1}$ (6) To a solution of the above product (7.3 g) in tetrahydrofuran (50 ml) is added conc. hydrochloric acid (5 ml), and the mixture is stirred at room temperature for one hour. To the mixture is added saturated aqueous sodium chloride solution, and the mixture is extracted with ethyl acetate. The extract is dried, concentrated under reduced pressure. The residue is purified by silica gel column chromatography (eluent; chloroform:methanol=20:1) to give (1Z,3E)-1-(4-cyclopentyloxy-3-methoxyphenyl)-2-methoxycarbonyl-3-carboxy-4-phenylbutadiene (6.1 g).

Yield: 92%

IR: 3500-3000 (br.), 2958, 1712, 1690, 1600, 1509, 1270, 694 cm$^{-1}$ (7) To a solution of the above product (0.75 g) in tetrahydrofuran (20 ml) is added carbonyldiimidazole (0.35 g), and the mixture is stirred at room temperature for 30 minutes. To the solution is added a 28% aqueous ammonia (0.7 ml), and the mixture is stirred at room temperature for 30 minutes. To the mixture is added water, and the mixture is extracted with chloroform. The extract is dried, and concentrated under reduced pressure. The residue is purified by silica gel column chromatography (eluent; chloroform:acetone=5:1) to give (1Z,3E)-1-(4-cyclopentyloxy-3-methoxyphenyl)-2-methoxycarbonyl-3-aminocarbonyl-4-phenylbutadiene (0.48 g). The structure and the physical properties thereof are shown in Table 1.

Yield: 64%

M.p. 158–159° C.

EXAMPLE 2

(1) To a solution of the compound obtained in Example 1-(6) (0.3 g) in dichloromethane (10 ml) are added triethylamine (0.15 ml) and isobutyl chloroformate (0.14 ml) at 0° C., and the mixture is stirred for 30 minutes. To the solution is added 4-picolylamine (0.11 ml), and the mixture is stirred for 30 minutes. Water is added to the mixture, and the mixture is extracted with chloroform. The extract is dried, concentrated under reduced pressure, and the residue is purified by silica gel column chromatography (eluent; chloroform: methanol=50:1) to give (1Z,3E)-1-(3-methoxy-4-cyclopentyloxyphenyl)-2-methoxycarbonyl-3-(4-pyridylmethylaminocarbonyl)-4-phenylbutadiene (0.29 g).

Yield: 80%

(2) To the above product (0.29 g) is added a 4N solution of hydrogen chloride in ethyl acetate, and the mixture is triturated with ether to give (1Z,3E)-1-(3-methoxy-4-cyclopentyloxyphenyl)-2-methoxycarbonyl-3-(4-pyridyl-methylaminocarbonyl)-4-phenylbutadiene hydrochloride (0.29 g). The structure and the physical properties thereof are shown in Table 1.

Yield: 93%

M.p. 105–130° C.

EXAMPLES 3–4

The corresponding starting compounds are treated in the same manner as in Example 2 to give the compounds as listed in Table 1.

TABLE 1

| Ex. No. | —R | Physical properties |
|---|---|---|
| 1 | —H | M.p. 158–159° C. |
| 2 | —CH$_2$—(4-pyridyl) | M.p. 105–130° C. monohydrochloride |
| 3 | —CH$_2$—(2-pyridyl) | M.p. 85–115° C. monohydrochloride |
| 4 | —CH$_2$—(3-pyridyl) | M.p. 80–115° C. monohydrochloride |

EXAMPLE 5

To a solution of the compound obtained in Example 1-(7) (0.28 g) in tetrahydrofuran (10 ml) is added a 2N aqueous sodium hydroxide solution (1 ml), and the mixture is stirred at room temperature for 10 minutes. The mixture is neutralized with 2N hydrochloric acid, and extracted with chloroform. The extract is dried, concentrated under reduced pressure, and the residue is purified by silica gel column chromatography (eluent; hexane:ethyl acetate=2:1) to give (3Z,4E)-4-benzylidene-3-(4-cyclopentyloxy-3-methoxybenzylidene)-pyrrolidine-2,5-dione (0.24 g). The structure and the physical properties thereof are shown in Table 2.

EXAMPLE 6

(1) To a solution of the compound obtained in Example 2-(2) (0.25 g) in tetrahydrofuran (10 ml) is added a 2N aqueous sodium hydroxide solution (1.1 ml), and the mixture is stirred at room temperature. To the mixture is added water, and the mixture is extracted with chloroform. The extract is dried, and concentrated under reduced pressure to remove the solvent. The residue is purified by silica gel column chromatography (eluent; ethyl acetate:hexane=1:1) to give (3Z,4E)-3-(4-cyclopentyloxy-3-methoxybenzylidene)-4-benzylidene-1-(4-pyridylmethyl)pyrrolidine-2,5-dione (0.12 g).

Yield: 55%

(2) To the above product (0.12 g) is added a 4N solution of hydrogen chloride in dioxane, and the mixture is triturated with ether to give (3Z,4E)-3-(4-cyclopentyloxy-3-methoxybenzylidene)-4-benzylidene-1-(4-pyridylmethyl)pyrrolidine-2,5-dione hydrochloride (90 mg). The structure and the physical properties thereof are shown in Table 2.

Yield: 76%

M.p. 117–130° C. (decomposed)

EXAMPLES 7–8

The corresponding starting compounds are treated in the same manner as in Example 6 to give the compound as listed in Table 2.

EXAMPLE 9

(1) To a solution of the compound obtained in Example 1-(6) (0.3 g) in dichloromethane (10 ml) are added triethylamine (0.15 ml) and isobutyl chloroformate (0.14 ml) at 0° C., and the mixture is stirred for 30 minutes. To the mixture is added N,N-dimethylethylenediamine (0.12 ml), and the mixture is stirred for 30 minutes. To the mixture is added water, and the mixture is extracted with chloroform. The extract is dried and concentrated under reduced pressure. To the residue are added tetrahydrofuran (5 ml) and a 2N aqueous sodium hydroxide solution (0.7 ml), and the mixture is stirred at room temperature for 10 minutes. To the mixture is added water, and the mixture is extracted with chloroform. The extract is dried, and concentrated under reduced pressure. The residue is purified by silica gel column chromatography (eluent; chloroform:methanol= 20:1) to give (3Z,4E)-3-(4-cyclopentyloxy-3-methoxybenzylidene)-4-benzylidene-1-(2-(N,N-dimethylamino)ethyl)pyrrolidine-2,5-dione (0.25 g).

Yield: 76%

(2) To the above product (0.25 g) is added a 4N solution of hydrogen chloride in ethyl acetate, and the mixture is triturated with ether to give (3Z,4E)-3-(4-cyclopentyloxy-3-methoxybenzylidene)-4-benzylidene-1-(2-(N,N-dimethylamino)ethyl)pyrrolidine-2,5-dione hydrochloride (0.17 g). The structure and the physical properties thereof are shown in Table 2.

Yield: 88%

M.p. 95–110° C. (decomposed)

EXAMPLE 10

The corresponding starting compounds are treated in the same manner as in Example 9 to give the compound as listed in Table 2.

TABLE 2

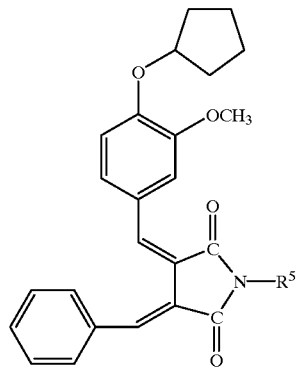

| Ex. No. | —R⁵ | Physical properties |
| --- | --- | --- |
| 5 | —H | M.p. 203–204° C. |
| 6 | —CH₂-(4-pyridyl) | M.p. 117–130° C. (decomp.) monohydrochloride |
| 7 | —CH₂-(2-pyridyl) | M.p. 110–116° C. (decomp.) monohydrochloride |
| 8 | —CH₂-(3-pyridyl) | M.p. 105–125° C. (decomp.) monohydrochloride |
| 9 | —(CH₂)₂N(CH₃)₂ | M.p. 95–110° C. (decomp.) monohydrochloride |
| 10 | —(CH₂)₂OH | M.p. 133–134° C. (decomp.) |

EXAMPLE 11

(1) To a solution of methyl magnesium iodide, which is prepared from magnesium (2.9 g) and methyl iodide (7.5 ml), in diethyl ether (150 ml) is added dropwise a solution of 4-cyclopentyloxy-3-methoxybenzaldehyde (17.6 g) in tetrahydrofuran (40 ml) at 0° C., and the mixture is stirred at room temperature for one hour. To the reaction mixture is added a saturated aqueous ammonium chloride solution (20 ml) at 0° C., and the mixture is extracted with ethyl acetate. The extract is concentrated under reduced pressure, and the residue is dissolved in acetonitrile (300 ml), and thereto is added manganese dioxide (55 g) at 0° C. The mixture is warmed to room temperature, and the mixture is stirred for three days. To the reaction mixture is added cerite (20 g), and the mixture is stirred for 30 minutes. The insoluble materials are removed by filtration, and the filtrate is concentrated under reduced pressure. The residue is crystallized from chilled hexane to give 4-acetyl-1-cyclopentyloxy-2-methoxybenzene (13.8 g).

Yield: 73.6%

M.p. 55–56° C.

(2) A solution of the above product (9.7 g) and dimethyl (E)-benzylidenesuccinate (10 g) in tetrahydrofuran (100 ml) is added dropwise into a solution of potassium tert-butoxide (4.8 g) in tert-butyl alcohol (100 ml) at room temperature, and the mixture is stirred at the same temperature for one hour. To the reaction mixture is added diisopropyl ether (200 ml), and the mixture is extracted with water. The pH value of the aqueous layer is adjusted to pH 1–2 with conc. hydrochloric acid, and the mixture is extracted again with ethyl acetate. The extract is concentrated under reduced pressure, and the ⅔ part of the residue is collected, and dissolved in chloroform (100 ml). To the mixture are added a few drops of N,N-dimethylformamide and thionyl chloride (1.8 ml) at room temperature, and the mixture is refluxed for 30 minutes. The reaction mixture is cooled with ice, and added dropwise into a solution of aqueous ammonia (20 ml) in chloroform (50 ml), and the mixture is stirred for 30 minutes. Water (50 ml) is added to the reaction mixture, and then the mixture is extracted with chloroform. The extract is concentrated under reduced pressure to remove the solvent, and the residue is purified by silica gel column chromatography (eluent; chloroform:acetone=20:1), and crystallized from hexane-ethyl acetate to give (1Z,3E)-1-methyl-1-(4-cyclopentyloxy-3-methoxyphenyl)-2-methoxycarbonyl-3-aminocarbonyl-4-phenylbutadiene (0.42 g). The structure and the physical properties thereof are shown in Table 3.

M.p. 133–134° C.

EXAMPLES 12–22

The corresponding starting compounds are treated in the same manner as in Example 11 to give the compounds as listed in Tables 3–5.

TABLE 3

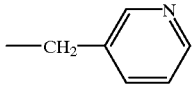

| Ex. No. | —R | Physical properties |
|---|---|---|
| 11 | —H | M.p. 133–134° C. |
| 12 | —CH$_2$-(2-pyridyl) | M.p. 85–105° C. (decomp.) monohydrochloride |
| 13 | —CH$_2$-(3-pyridyl) | M.p. 100–104° C. (decomp.) monohydrochloride |
| 14 | —CH$_2$-(4-pyridyl) | M.p. 106–114° C. (decomp.) monohydrochloride |

TABLE 3-continued

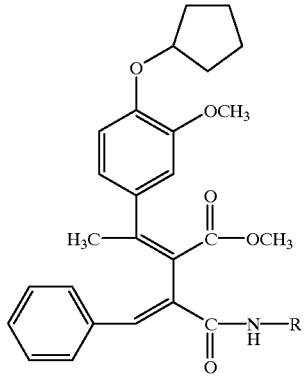

| Ex. No. | —R | Physical properties |
|---|---|---|
| 15 | —N(CH$_3$)$_2$ | |

TABLE 4

| Ex. No. | —R | Physical properties |
|---|---|---|
| 16 | —H | M.p. 166–167° C. |
| 17 | —CH$_2$-(2-pyridyl) | M.p. 132–133° C. (decomp.) monohydrochloride |
| 18 | —CH$_2$-(3-pyridyl) | M.p. 127–128° C. (decomp.) monohydrochloride |
| 19 | —CH$_2$-(4-pyridyl) | M.p. 114–115° C. (decomp.) monohydrochloride |
| 20 | —N(CH$_3$)$_2$ | M.p. 88–89° C. |

TABLE 5

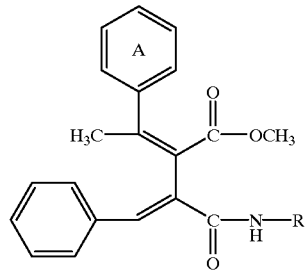

| Ex. No. | Ring A | —R | Physical properties |
|---|---|---|---|
| 21 | 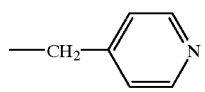 | 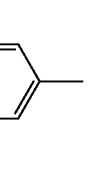 | monohydrochloride |
| 22 | 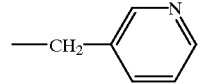 | 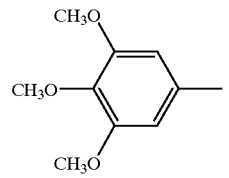 | M.p. >90° C. (decomp.) monohydrochloride |
| 23 (3) | (same as Ex. 23 structure, 3,4,5-trimethoxyphenyl) | —H | M.p. 118–120° C. |

EXAMPLE 23

(1) To a solution of potassium tert-butoxide (2.4 g) in tert-butyl alcohol (25 ml) is added dropwise a solution of 3,4,5-trimethoxyacetophenone (5.0 g) and dimethyl (E)-benzylidene succinate (4.5 g) in tetrahydrofuran (20 ml) at 20–25° C., and the mixture is stirred at room temperature for one hour. The reaction mixture is poured into water, and the mixture is washed with diisopropyl ether. The pH value of the aqueous layer is adjusted to pH 1 with hydrochloric acid, and extracted with ethyl acetate. The extract is dried, and concentrated under reduced pressure, and the residue is purified by silica gel column chromatography (eluent; chloroform:methanol=50:1→20:1) to give 1-methyl-1-(3,4,5-trimethoxyphenyl)-2-methoxycarbonyl-3-carboxy-4-phenylbutadiene (6.5 g) as a mixture of (1E,3E)-isomer and (1Z,3E)-isomer.

Yield: 66.3%

IR: 3420, 2950, 1720, 1715, 1690, 1585, 1240, 1125, 695 cm$^{-1}$ (2) To a solution of the above product (6.5 g) in chloroform (30 ml) are added a few drops of N,N-dimethylformamide and thionyl chloride (1.15 ml), and the mixture is refluxed for 30 minutes. The solution is added dropwise into conc. aqueous ammonia (20 ml) at 0° C., and the mixture is stirred at room temperature for 30 minutes. The mixture is extracted with chloroform, and the extract is dried, concentrated under reduced pressure, and the residue is purified by silica gel column chromatography (eluent; hexane:ethyl acetate=1:1→1:2). The eluent is concentrated and crystallized from ether, and the precipitated crystals are collected by filtration, and further recrystallized from hexane-ethyl acetate to give (1E,3E)-1-methyl-1-(3,4,5-trimethoxyphenyl)-2-methoxycarbonyl-3-aminocarbonyl-4-phenylbutadiene (2.6 g). The structure and the physical properties thereof are shown in Table 6.

Yield: 40.1%

M.p. 155–157° C.

(3) The filtrate obtained in the above (2) is concentrated under reduced pressure, and the residue is crystallized from diisopropyl ether, and then recrystallized from hexane-ethyl acetate to give (1Z,3E)-1-methyl-1-(3,4,5-trimethoxyphenyl)-2-methoxycarbonyl-3-aminocarbonyl-4-phenylbutadiene (2.1 g). The structure and the physical properties are shown in Table 5.

Yield: 32.4%

M.p. 118–120° C.

EXAMPLE 24

(1) To a solution of potassium tert-butoxide (14.5 g) in tert-butyl alcohol (100 ml) is added a mixture of acetophenone (15.5 g) and dimethyl succinate (27.1 g), and the mixture is stirred at room temperature overnight. The reaction mixture is poured into ice-water, and the mixture is washed with diisopropyl ether. The pH value of the aqueous layer is adjusted to pH 2–3 with conc. hydrochloric acid, and then extracted with ethyl acetate. The extract is dried, and concentrated under reduced pressure. The residue is dissolved in methanol (150 ml), and thereto is added dropwise thionyl chloride (12.5 ml) under ice-cooling. The mixture is stirred at room temperature overnight, and concentrated under reduced pressure to remove the solvent. The residue is washed with ethyl acetate, dried, and concentrated under reduced pressure to remove the solvent. The resulting residue is purified by silica gel column chromatography (eluent; hexane:ethyl acetate=4:1) to give (E)-2-benzylidene-α-methylsuccinic acid dimethyl ester (18.6 g) and (Z)-2-benzylidene-α-methyl-succinic acid dimethyl ester (6.2 g).

(E)-2-Benzylidene-α-methylsuccinic acid dimethyl ester

Yield: 58%

Oily product

IR: 2970, 2940, 2860, 1745, 1440, 1270, 1200, 1180, 1135, 1060, 770, 705 cm$^{-1}$ (Z)-2-Benzylidene-α-methylsuccinic acid dimethyl ester Yield: 19%

Oily product

IR: 2960,2920,2850, 1740, 1710, 1440, 1320,1250, 1195, 1170, 1140, 765, 700 cm$^{-1}$ (2) A solution of (E)-2-benzylidene-α-methylsuccinic acid dimethyl ester (5.0 g) and 3,4,5-trimethoxybenzaldehyde (4.0 g) in tetrahydrofuran (20 ml) is added dropwise into a solution of potassium tert-butoxide (2.3 g) in tert-butyl alcohol (20 ml), and the mixture is stirred at room temperature for one hour. The reaction mixture is poured into ice-water, and the mixture is washed. The pH value of the aqueous layer is adjusted to pH 2–3 with conc. hydrochloric acid, and the mixture is extracted with ethyl acetate. The extract is dried, concentrated under reduced pressure, and the resulting residue is dissolved in chloroform (30 ml). To the mixture are added thionyl chloride (1.5 ml) and three drops of N,N-dimethylformamide, and the mixture is refluxed for 30 minutes. The mixture is added dropwise into a 28% aqueous ammonia (20 ml) under ice-cooling, and the mixture is stirred at room temperature for 10 minutes. Water is added to the mixture, and extracted with chloroform. The extract is dried and concentrated under reduced pressure to remove the solvent. The residue is purified by silica gel column chromatography (eluent; hexane: ethyl acetate=1:1) to give (1E,3E)-1-(3,4,5-trimethoxyphenyl)-2-methoxycarbonyl-3-aminocarbonyl-4-methyl-4-phenylbutadiene (4.7 g). The structure and the physical properties thereof are shown in Table 6.

Yield: 57%

M.p. 156–157° C.

TABLE 6

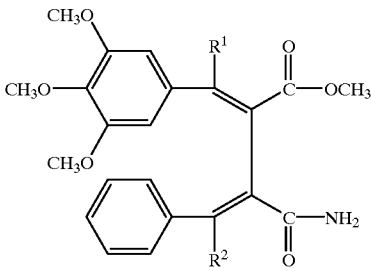

| Ex. No. | —R$^1$ | —R$^2$ | Physical properties |
|---|---|---|---|
| 23 (2) | —CH$_3$ | —H | M.p. 155–157° C. |
| 24 | —H | —CH$_3$ | M.p. 156–157° C. |

EXAMPLE 25

(Z)-2-Benzylidene-α-methylsuccinic acid dimethyl ester (5.3 g) obtained in Example 24-(1) is treated in the same manner as in Example 24-(2) to give (1E,3Z)-1-(3,4,5-trimethoxyphenyl)-2-methoxycarbonyl-3-aminocarbonyl-4-methyl-4-phenylbutadiene (6.7 g). The structure and the physical properties thereof are shown in Table 7.

Yield: 76%

M.p. 141–143° C.

TABLE 7

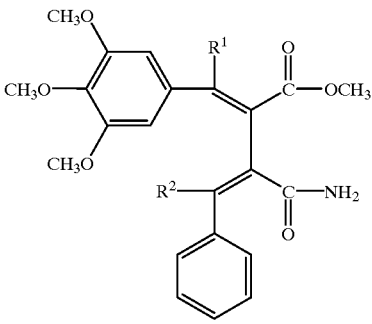

| Ex. No. | —R$^1$ | —R$^2$ | Physical properties |
|---|---|---|---|
| 25 | —H | —CH$_3$ | M.p. 141–143° C. |

EXAMPLE 26

To a solution of the compound (0.32 g) obtained in Example 11-(2) in tetrahydrofuran (20 ml) is added a 2N aqueous sodium hydroxide solution (3.6 ml) at 0° C., and the mixture is stirred for 10 minutes. To the reaction mixture is added 2N hydrochloric acid (3.6 ml), and the mixture is extracted with ethyl acetate. The extract is concentrated under reduced pressure to remove the solvent, and the residue is purified by silica gel column chromatography (eluent; chloroform:acetone=10:1), and further crystallized from diethyl ether to give (3Z,4E)-4-benzylidene-3-(4-cyclopentyloxy-3-methoxy-α-methylbenzylidene) pyrrolidine-2,5-dione (0.17 g). The structure and the physical properties thereof are shown in Table 8.

Yield: 58.0%

M.p. 193–194° C.

EXAMPLES 27–38

The corresponding starting compounds are treated in the same manner as in Example 26 to give the compounds as listed in Tables 8–10.

TABLE 8

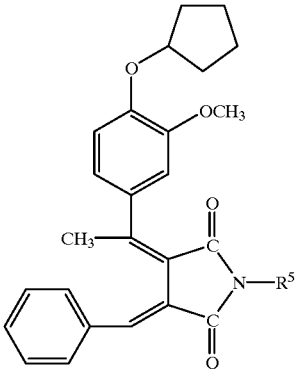

| Ex. No. | —R$^5$ | Physical properties |
|---|---|---|
| 26 | —H | M.p. 193–194° C. |
| 27 | 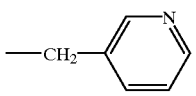 —CH$_2$— (2-pyridyl) | M.p. 120–125° C. (decomp.) monohydrochloride |
| 28 | 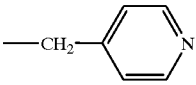 —CH$_2$— (3-pyridyl) | M.p. 199–200° C. monohydrochloride |
| 29 | 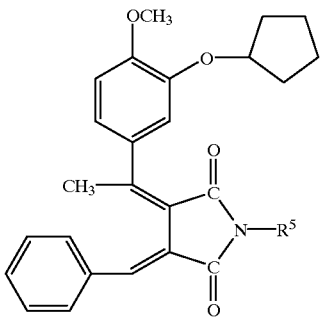 —CH$_2$— (4-pyridyl) | M.p. 204–205° C. monohydrochloride |
| 30 | —N(CH$_3$)$_2$ | |

TABLE 9

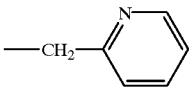

| Ex. No. | —R$^5$ | Physical properties |
|---|---|---|
| 31 | —H | |
| 32 | 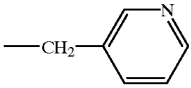 —CH$_2$— (2-pyridyl) | monohydrochloride |
| 33 | —CH$_2$— (3-pyridyl) | M.p. 121–122° C. (decomp.) monohydrochloride |
| 34 | 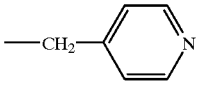 —CH$_2$— (4-pyridyl) | M.p. 136–137° C. (decomp.) monohydrochloride |
| 35 | —N(CH$_3$)$_2$ | |

TABLE 10
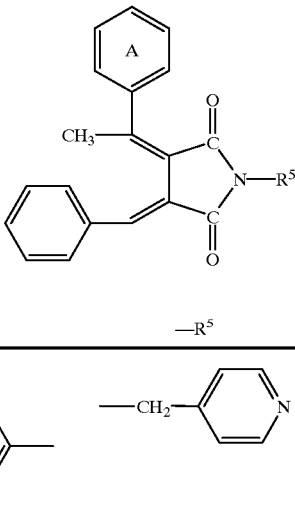
| Ex. No. | Ring A | —R[5] | Physical properties |
|---|---|---|---|
| 36 | 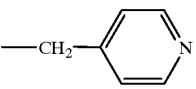 | 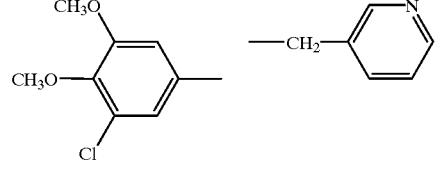 | M.p. 127° C. monohydrochloride |
| 37 | 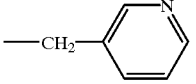 | 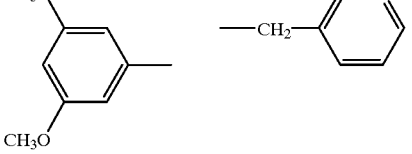 | M.p. >145° C. (decomp.) monohydrochloride |
| 38 | 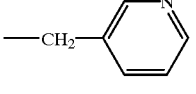 | 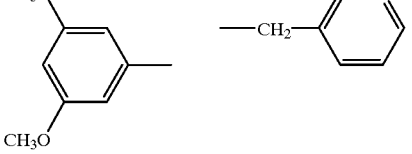 | M.p. 60° C. monohydrochloride |
EXAMPLES 39–43
The corresponding starting compounds are treated in the same manner as in Example 1 to give the compounds as listed in Table 11.

TABLE 11
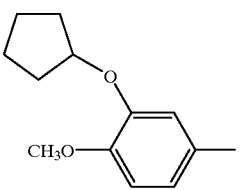
| Ex. No. | Ring A | Physical properties |
|---|---|---|
| 39 | 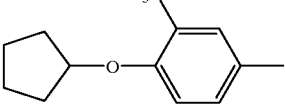 | M.p. 134–135° C. monohydrochloride |
| 40 | 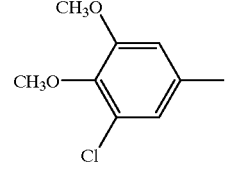 | M.p. 100–108° C. (decomp.) monohydrochloride |
| 41 | 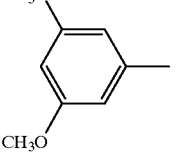 | monohydrochloride |
| 42 | 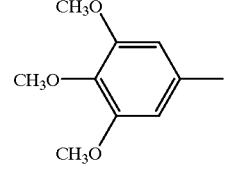 | monohydrochloride |
| 43 | | monohydrochloride |
EXAMPLES 44–48
The corresponding starting compounds are treated in the same manner as in Example 5 to give the compounds as listed in Table 12.

TABLE 12

| Ex. No. | Ring A | Physical properties |
|---|---|---|
| 44 | cyclopentyl-O, CH₃O-phenyl | monohydrochloride |
| 45 | CH₃O, cyclopentyl-O-phenyl | M.p. 220–240° C. (decomp.) monohydrochloride |
| 46 | CH₃O, CH₃O, Cl-phenyl | monohydrochloride |
| 47 | CH₃O, CH₃O-phenyl (3,5) | monohydrochloride |
| 48 | CH₃O, CH₃O, CH₃O-phenyl | monohydrochloride |

EXAMPLE 49

(1) Vanillin (100 g) is dissolved in chloroform (800 ml), and thereto is blown with stirring chlorine gas at room temperature for about one hour to give the white solid. The compressed air is blown into the mixture to remove the chlorine being dissolved therein, and the precipitated solid is collected by filtration, washed, and dried. The mother liquor is concentrated, and triturated with diethyl ether, and the precipitates are collected by filtration, washed, and dried. The former precipitated solid and the powder thus obtained are combined to give 3-chlorovanillin (115.25 g).

Yield: 94.0%

M.p. 163° C.

(2) The above product (62 g) is dissolved in N,N-dimethylformamide (600 ml), and thereto are added potassium carbonate (91.8 g) and methyl iodide (37.2 ml) at room temperature, and the mixture is stirred at the same temperature for five hours. The reaction mixture is concentrated, and thereto is added water. The mixture is extracted with ethyl acetate, and the ethyl acetate layer is washed, dried, and concentrated under reduced pressure to remove the solvent to give 3-chloro-4,5-dimethoxybenzaldehyde (65.15 g).

Yield: 97.7%

M.p. 54° C.

(3) To a solution of magnesium (11.87 g) in diethyl ether (500 ml) is added gradually and dropwise a solution of methyl iodide (30.4 ml) in diethyl ether (100 ml) under nitrogen atmosphere. After the addition, the mixture is stirred for 30 minutes until the reflux is completed. To the mixture is added dropwise a solution of the compound (70 g) obtained in the above (2) in tetrahydrofuran (400 ml) under ice-cooling. The mixture is warmed to room temperature, and further stirred for 30 minutes. To the reaction mixture is added a small amount of water, and the reaction is quenched. To the reaction mixture is added an aqueous ammonium chloride solution, and the mixture is extracted with ethyl acetate. The ethyl acetate layer is washed, dried, and concentrated under reduced pressure to remove the solvent to give 3-chloro-4,5-dimethoxy-1-(1-hydroxyethyl)benzene (75 g).

The above product (75 g) is dissolved in acetonitrile (500 ml), and thereto is added manganese dioxide (400 g), and the mixture is stirred at room temperature overnight. Cerite is added to the reaction mixture, and the mixture is stirred for one hour. The mixture is filtered through cerite pad, and the mother liquor is concentrated. The residue is purified by silica gel column chromatography (eluent; hexane:ethyl acetate=3:1), and recrystallized from hexane to give 3-chloro-4,5-dimethoxyacetophenone (62.0 g).

Yield: 82.8%

M.p. 47–49° C.

(4) A solution of the above product (11.3 g) in dimethyl succinate (11.54 g) in tetrahydrofuran (50 ml) is added gradually and dropwise into a solution of potassium tert-butoxide (6.5 g) in t-butyl alcohol (30 ml) at room temperature. The mixture is stirred at room temperature for one hour, warmed to 70° C., and then stirred for one hour. The reaction mixture is cooled, and poured into ice-water, and further dissolved in isopropyl ether to purification, and then the mixture is extracted with water. The pH value of the aqueous layer is adjusted to pH 2–3 with conc. hydrochloric acid, and the free carboxylic acid is extracted with ethyl acetate. The extract is dried, and concentrated under reduced pressure to give 4-(3-chloro-4,5-dimethoxyphenyl)-4-methyl-3-methoxycarbonyl-3-butenoic acid as an amber oil.

The product thus obtained is dissolved in dichloromethane (100 ml), and thereto are added diisopropyl ethylamine (11.0 ml) and methoxymethyl chloride (4.8 ml) at 0° C., and the mixture is stirred at room temperature overnight. The reaction mixture is concentrated, and thereto is added aqueous citric acid solution, and then extracted with ethyl acetate. The extract is washed, dried, and concentrated under reduced pressure. The residue is purified by silica gel column chromatography (eluent; ethyl acetate:hexane= 1:3→2:3) to give (Z)-4-(3-chloro-4,5-dimethoxyphenyl)-4-methyl-3-methoxycarbonyl-3-butenoic acid methoxymethyl ester (3.18 g) and (E)-4-(3-chloro-4,5-dimethoxyphenyl)-4-methyl-3-methoxycarbonyl-3-butenoic acid methoxymethyl ester (9.12 g). (Z)-4-(3-Chloro-4,5-dimethoxyphenyl)-4-methyl-3-methoxycarbonyl-3-butenoic acid methoxymethyl ester Yield: 16.2%

IR: 1735, 1563, 1491, 1148, 932 cm$^{-1}$ (E)-4-(3-Chloro-4,5-dimethoxyphenyl)-4-methyl-3-methoxycarbonyl-3-butenoic acid methoxymethyl ester Yield: 46.5%

IR: 1738, 1562, 1491, 1146, 932 cm$^{-1}$ (5) To a solution of diisopropylamine (1.33 ml) in tetrahydrofuran (20 ml) is added gradually and dropwise a 1.6 N solution of n-butyl lithium in hexane (5.91 ml) at 0° C., and the mixture is stirred at the same temperature for 30 minutes. The solution is cooled to −78° C., and thereto is added gradually and dropwise a solution of (Z)-4-(3-chloro-4,5-dimethoxyphenyl)-4-methyl-3-methoxycarbonyl-3-butenoic acid methoxymethyl ester (2.94 g) in tetrahydrofuran (20 ml), and the mixture is further stirred at the same temperature for 30 minutes. The reaction mixture is cooled to −90° C., and thereto is added gradually and dropwise a solution of isonictinaldehyde (1.01 g) in tetrahydrofuran (10 ml), and the mixture is stirred at −90° C. for 20 minutes. To the reaction mixture is added a saturated aqueous ammonium chloride solution, and the mixture is extracted with ethyl acetate. The organic layer is washed, dried, and concentrated under reduced pressure to remove the solvent to give (Z)-4-(3-chloro-4,5-dimethoxyphenyl)-4-methyl-3-methoxycarbonyl-2-(4-pyridylhydroxymethyl)-3-butenoic acid methoxymethyl ester.

The above product is dissolved in dichloromethane (50 ml), and thereto are added triethylamine (7.54 ml) and methanesulfonyl chloride (0.977 ml) at 0° C. The mixture is warmed to room temperature, and stirred overnight. To the mixture is added 1,8-diazabicyclo[5.4.0]undeca-7-ene (DBU, 1.18 ml), and the mixture is stirred at room temperature for 3 hours. The reaction mixture is concentrated, and thereto is added water. The mixture is extracted with ethyl acetate, washed, dried and concentrated under reduced pressure to remove the solvent. The residue is purified by silica gel column chromatography (eluent; chloroform:acetone= 6:1) to give (1Z,3E)-1-methyl-1-(3-chloro-4,5-dimethoxyphenyl)-2-methoxycarbonyl-3-methoxymethoxycarbonyl-4-(4-pyridyl)butadiene (2.007 g).

Yield: 55.1%

IR: 1720, 1594, 1563, 1490, 1253, 1047, 927 cm$^{-1}$ (6) To a solution of the above product (2.0 g) in tetrahydrofuran (20 ml) is added 12 N hydrochloric acid (2.0 ml) at 0° C., and the mixture is stirred at room temperature for two hours. The reaction mixture is cooled with ice, and the pH value thereof is adjusted to pH 4–5 with 2N aqueous sodium hydroxide solution, and the mixture is extracted with ethyl acetate. The extract is dried, and concentrated under reduced pressure to give (1Z,3E)-1-methyl-1-(3-chloro-4,5-dimethoxyphenyl)-2-methoxycarbonyl-3-carboxy-4-(4-pyridyl)butadiene as a yellow solid.

The above product is dissolved in dichloromethane (20 ml), and thereto are added triethylamine (0.67 ml) and isobutyl chloroformate (0.62 ml) under ice-cooling. The mixture is stirred at the same temperature for 30 minutes, and thereto is added a 28% aqueous ammonia (2.8 ml) at 0° C. The mixture is stirred at 0° C. for 30 minutes. The 2-fold diluted, saturated aqueous sodium chloride solution is added to the reaction mixture, and the mixture is extracted with chloroform. The extract is dried, concentrated under reduced pressure, and the resulting residue is purified by silica gel column chromatography (eluent; chloroform:methanol= 20:1) to give 1-methyl-1-(3-chloro-4,5-dimethoxyphenyl)-2-methoxycarbonyl-3-aminocarbonyl-4-(4-pyridyl) butadiene (1.498 g).

Yield: 83.0%

IR: 1720, 1676, 1595, 1240, 1047, 999, 855 cm$^{-1}$

The product thus obtained is in the form of a mixture of stereoisomers based on the double bond at 1-position, and the ratio of the Z-isomer and E-isomer is 2.5:1.

(7) The above product is purified and separated by silica gel column chromatography (eluent; chloroform:acetone= 5:1) to give (1Z,3E)-1-methyl-1-(3-chloro-4,5-dimethoxyphenyl)-2-methoxycarbonyl-3-aminocarbonyl-4-(4-pyridyl)butadiene. The structure and the physical properties thereof are shown in Table 13.

EXAMPLES 50–53

The corresponding starting compounds are treated in the same manner as in Example 49 to give the compounds as listed in Table 13.

TABLE 13

[Structure: Ring A connected via C=C(CH3) to C(=O)OCH3 and via CH= (from pyridine) to C(=O)NH2]

| Ex. No. | Ring A | Physical properties |
|---|---|---|
| 49 | 3-chloro-4,5-dimethoxyphenyl (CH3O, CH3O, Cl substituents) | IR: (cm⁻¹) 1720, 1676, 1595, 1240, 1047, 999, 855 |
| 50 | 3-cyclopentyloxy-4-methoxyphenyl | M.p. 177–178° C. (decomp.) monohydrochloride |
| 51 | 4-cyclopentyloxy-3-methoxyphenyl | M.p. 154–157° C. (decomp.) monohydrochloride |
| 52 | 3,5-dimethoxyphenyl | M.p. 172–175° C. monohydrochloride |
| 53 | 3,4,5-trimethoxyphenyl | M.p. 87–89° C. monohydrochloride |

EXAMPLE 54

(1) The compound (800 mg) obtained in Example 49-(7) is dissolved n tetrahydrofuran (20 ml), and thereto is added a 2N aqueous sodium hydroxide solution (0.48 ml) under ice-cooling. The mixture is warmed to room temperature and stirred for one hour. To the reaction mixture are added water, and the mixture is extracted with chloroform. The extract is washed, dried, and concentrated under reduced pressure. The residue is purified by silica gel column chromatography (eluent: chloroform:methanol=20:1), and further recrystallized from a mixture of hexane and ethyl acetate to give (3Z,4E)-3-(3-chloro-4,5-dimethoxy-α-methylbenzylidene)-4-(4-pyridylmethylidene)pyrrolidine-2,5-dione (82 mg).

Yield: 11.1%

M.p. >194° C. (decomposed)

IR: 1721, 1599, 1491, 1328, 1049 cm⁻¹

(2) The above product (75 mg) is dissolved in a mixture of tetrahydrofuran (1 ml) and dioxane (1 ml), and thereto is added a 4N solution of hydrogen chloride in dioxane (0.054 ml), and the mixture is stirred at room temperature for crystallization to give a pale yellow solid. The mixture is concentrated under reduced pressure to remove the solvent, and the residue is triturated with diethyl ether, and the resultant is further stirred in a mixture of methanol and diethyl ether at room temperature to crystallize to give (3Z,4E)-3-(3-chloro-4,5-dimethoxy-α-methylbenzylidene)-4-(4-pyridylmethylidene)pyrrolidine-2,5-dione hydrochloride (70 mg). The structure and the physical properties thereof are shown in Table 14.

Yield: 85.3%

M.p. >200° C. (decomposed)

IR: 1728, 1634, 1491, 1312 cm⁻¹

EXAMPLES 55–58

The corresponding starting compounds are treated in the same manner as in Example 54 to give the compounds as listed in Table 14.

TABLE 14

[Structure: pyrrolidine-2,5-dione with 3-(Ring A-C(CH3)=) and 4-(4-pyridyl-CH=) substituents]

| Ex. No. | Ring A | Physical properties |
|---|---|---|
| 54 | 3-chloro-4,5-dimethoxyphenyl (CH3O, CH3O, Cl) | M.p. >200° C. (decomp.) IR: (cm⁻¹) 1728, 1634, 1491, 1312 monohydrochloride |
| 55 | 3-cyclopentyloxy-4-methoxyphenyl | M.p. 179–180° C. (decomp.) monohydrochloride |
| 56 | 4-cyclopentyloxy-3-methoxyphenyl | M.p. 205–207° C. (decomp.) monohydrochloride |

TABLE 14-continued

[Structure: Ring A substituted pyrrolidinedione with H3C and pyridyl groups]

| Ex. No. | Ring A | Physical properties |
|---|---|---|
| 57 | 3,5-di(CH3O)-phenyl | M.p. 134–135° C. monohydrochloride |
| 58 | 3,4,5-tri(CH3O)-phenyl | M.p. 125–129° C. monohydrochloride |

EXAMPLE 59

(1) To a solution of potassium tert-butoxide (16.8 g) in tert-butyl alcohol (150 ml) is added dropwise with stirring a solution of benzaldehyde (15.9 g) and dimethyl succinate (26.3 g) in tert-butyl alcohol (20 ml) at room temperature, and the mixture is stirred for 30 minutes. The reaction mixture is poured into ice-water (200 ml), and the mixture is extracted with isopropyl ether. The pH value of the aqueous layer is adjusted to pH 2–3, and extracted with ethyl acetate. The extract is washed, dried, and concentrated under reduced pressure. The residue is dissolved in a mixture of toluene (50 ml) and ethylene glycol monomethyl ether (50 ml), and thereto is added dropwise thionyl chloride (16.4 ml) at 0° C. The mixture is allowed to stand at room temperature overnight, and the mixture is concentrated under reduced pressure. The residue is purified by silica gel column chromatography (eluent; hexane: ethyl acetate=4:1) to give (E)-3-methoxycarbonyl-4-phenyl-3-butenoic acid 2-methoxyethyl ester (26.9 g).

Yield: 65%

(2) A solution of the above product (14 g) and 3-cyclopentyloxy-4-methoxybenzaldehyde (11.1 g) in tert-butyl alcohol (100 ml) is added dropwise into a solution of potassium tert-butoxide (6.2 g) in tert-butyl alcohol (40 ml) at room temperature, and the mixture is stirred at the same temperature for one hour. The reaction mixture is poured into water, and the mixture is extracted with diisopropyl ether. The pH value of the aqueous layer is adjusted to pH 2–3 with hydrochloric acid, and extracted with ethyl acetate. The extract is washed, dried, and concentrated under reduced pressure to remove the solvent. The residue is washed with diethyl ether to give (E)-2-[(E)-3-cyclopentyloxy-4-methoxybenzylidene]-3-carboxy-4-phenyl-3-butenoic acid methyl ester (23.4 g).

Yield: 67%

(3) To a solution of the above product (5.0 g) in chloroform (100 ml) are added a few drops of N,N-dimethylformamide and thionyl chloride (0.82 ml), and the mixture is refluxed for 30 minutes. The solution is added dropwise with vigorously stirring into 2-picolylamine under ice-cooling. The mixture is further stirred for 30 minutes, and the organic layer is separated, washed, dried and concentrated under reduced pressure. The residue is purified by silica gel column chromatography (eluent; chloroform:acetone=5:1) to give (1E,3E)-1-(3-cyclopentyloxy-4-methoxybenzylidene)-2-(2-methoxyethoxycarbonyl)-3-(2-pyridylmethylaminocarbonyl)-4-phenylbutadiene (2.7 g).

Yield: 24%

(4) To a solution of the above product (2.7 g) in tetrahydrofuran (20 ml) is added a 4N solution of hydrogen chloride in dioxane (1.33 ml), and the mixture is stirred for 10 minutes. The mixture is concentrated under reduced pressure to remove the solvent, and the residue is crystallized from isopropyl ether to give (1E,3E)-1-(3-cyclopentyloxy-4-methoxybenzylidene)-2-(2-methoxyethoxycarbonyl)-3-(2-pyridylmethylaminocarbonyl)-4-phenylbutadiene hydrochloride (1.9 g). The structure and the physical properties thereof are shown in Table 15.

Yield: 66%

M.p. 167–168° C.

EXAMPLES 60–85

The corresponding starting compounds are treated in the same manner as in Example 59 to give the compounds as listed in Tables 15–20.

TABLE 15

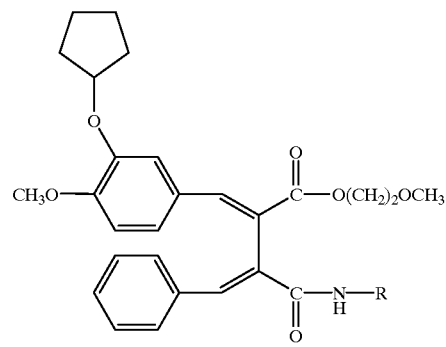

| Ex. No. | R | Physical properties |
|---|---|---|
| 59 | —CH2—(2-pyridyl) | M.p. 167–168° C. monohydrochloride |
| 60 | —CH2—(3-pyridyl) | M.p. 163–164° C. monohydrochloride |
| 61 | —CH2—(4-pyridyl) | M.p. 156–157° C. monohydrochloride |

TABLE 15-continued

[Structure: 3-cyclopentyloxy-4-methoxyphenyl and phenyl substituted diene with —C(O)O(CH₂)₂OCH₃ ester and —C(O)NH—R amide groups]

| Ex. No. | R | Physical properties |
|---|---|---|
| 62 | —N(CH₃)₂ | monohydrochloride |

TABLE 16

[Structure: 4-cyclopentyloxy-3-methoxyphenyl and phenyl substituted diene with —C(O)O(CH₂)₂OCH₃ ester and —C(O)NH—R amide groups]

| Ex. No. | R | Physical properties |
|---|---|---|
| 63 | —CH₂-(2-pyridyl) | M.p. 134–135° C. monohydrochloride |
| 64 | —CH₂-(3-pyridyl) | M.p. 142–144° C. monohydrochloride |
| 65 | —CH₂-(4-pyridyl) | M.p. 154–156° C. monohydrochloride |
| 66 | —N(CH₃)₂ | M.p. 81–83° C. monohydrochloride |

TABLE 17

[Structure: 3-chloro-4,5-dimethoxyphenyl and phenyl substituted diene with —C(O)OCH(CH₃)₂ ester and —C(O)NH—R amide groups]

| Ex. No. | R | Physical properties |
|---|---|---|
| 67 | —CH₂-(2-pyridyl) | M.p. 197–199° C. monohydrocliloride |
| 68 | —CH₂-(3-pyridyl) | M.p. >85° C. (decomp.) monohydrochloride |
| 69 | —CH₂-(4-pyridyl) | M.p. >102° C. (decomp.) monohydrochloride |
| 70 | —N(CH₃)₂ | M.p. >90° C. (decomp.) monohydrochloride |
| 71 | —(CH₂)₂N(CH₃)₂ | M.p. >83° C. (decomp.) monohydrochloride |

TABLE 18

[Structure: 3-chloro-4,5-dimethoxyphenyl and phenyl substituted diene with —C(O)O(CH₂)₂OCH₃ ester and —C(O)NH—R amide groups]

| Ex. No. | R | Physical properties |
|---|---|---|
| 72 | —CH₂-(2-pyridyl) | M.p. 200–202° C. monohydrochloride |
| 73 | —CH₂-(3-pyridyl) | Mp >65° C.(decomp.) monohydrochloride |
| 74 | —CH₂-(4-pyridyl) | M.p. >105° C. (decomp.) monohydrochloride |
| 75 | —N(CH₃)₂ | M.p. >70° C. (decomp.) monohydrochloride |

TABLE 19

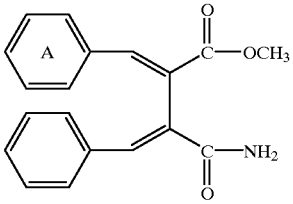

| Ex. No. | Ring A | Physical properties |
|---|---|---|
| 76 | 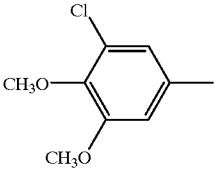 | M.p. 114–116° C. |
| 77 | 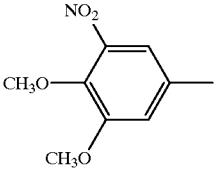 | M.p. 189–190° C. |
| 78 | 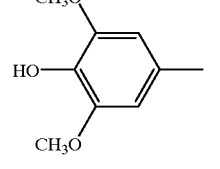 | M.p. 190–192° C. |
| 79 | 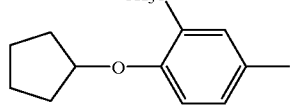 | M.p. 205–207° C. |
| 80 | 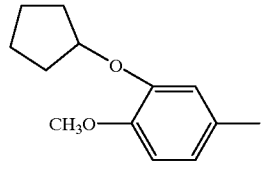 | M.p. 144–146° C. |
| 81 | 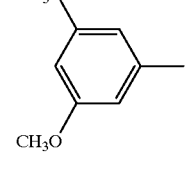 | M.p. 173–175° C. |
| 82 | 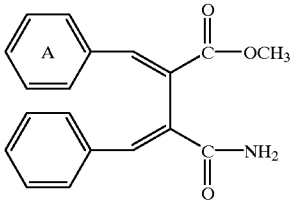 | M.p. 132–133° C. |

TABLE 19-continued

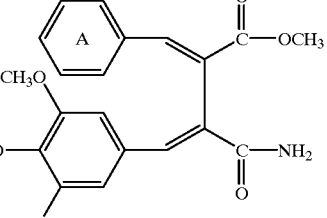

| Ex. No. | Ring A | Physical properties |
|---|---|---|
| 83 | 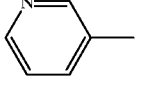 | M.p. 166–167° C. |

TABLE 20

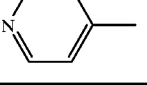

| Ex. No. | Ring A | Physical properties |
|---|---|---|
| 84 | (3-pyridyl) | M.p. 198° C. |
| 85 | (4-pyridyl) | M.p. 219° C. |

EXAMPLE 86

(1) To a solution of the compound (1.17 g) obtained in Example 59-(4) in tetrahydrofuran (10 ml) is added a 2N aqueous sodium hydroxide solution (10 ml), and the mixture is stirred at room temperature for 10 minutes. To the mixture is added 2N hydrochloric acid, and the mixture is concentrated under reduced pressure. Chloroform is added to the residue, and the mixture is washed, dried, and concentrated under reduced pressure to give (3E,4E)-3-(3-cyclopentyloxy-4-methoxybenzylidene)-4-benzylidene-1-(2-pyridylmethyl)pyrrolidine-2,5-dione (1.1 g).

Yield: 98%

(2) To a solution of the above product (1.1 g) in tetrahydrofuran (10 ml) is added a 4N solution of hydrogen chloride in dioxane (0.7 ml) at 0° C., and the mixture is stirred for 10 minutes. The mixture is concentrated under reduced pressure, and the residue is crystallized from ether to give (3E,4E)-3-(3-cyclopentyloxy-4-methoxybenzylidene)-4-benzylidene-1-(2 -pyridylmethyl)pyrrolidine-2,5-dione hydrochloride (1.1 g). The structure and the physical properties thereof are shown in Table 21.

Yield: 88%

M.p. 134–135° C.

EXAMPLES 87–103

The corresponding starting compounds are treated in the same manner as in Example 86 to give the compounds as listed in Tables 21–24.

TABLE 21

[Structure: 3-cyclopentyloxy-4-methoxyphenyl and phenyl bis-methylene pyrrolidine-2,5-dione with N-R⁵]

| Ex. No. | —R⁵ | Physical properties |
|---|---|---|
| 86 | —CH₂-(2-pyridyl) | M.p. 134–135° C. monohydrochloride |
| 87 | —CH₂-(3-pyridyl) | M.p. 92–93° C. (decomp.) monohydrochloride |
| 88 | —CH₂-(4-pyridyl) | M.p. 109–110° C.(decomp.) monohydrochloride |
| 89 | —(CH₂)₂N(CH₃)₂ | M.p. 96–97° C. monohydrochloride |
| 90 | —N(CH₃)₂ | M.p. 197–198° C. monohydrochloride |

TABLE 22

[Structure: 3-methoxy-4-cyclopentyloxyphenyl and phenyl bis-methylene pyrrolidine-2,5-dione with N-R⁵]

| Ex. No. | —R⁵ | Physical properties |
|---|---|---|
| 91 | —CH₂-(2-pyridyl) | M.p. 174–175° C. monohydrochloride |

TABLE 22-continued

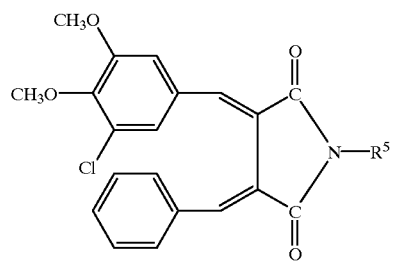

| Ex. No. | —R⁵ | Physical properties |
|---|---|---|
| 92 | —CH₂-(3-pyridyl) | M.p. 203–204° C. monohydrochloride |
| 93 | —CH₂-(4-pyridyl) | M.p. 216–217° C. monohydrochloride |

TABLE 23

[Structure: 3-chloro-4,5-dimethoxyphenyl and phenyl bis-methylene pyrrolidine-2,5-dione with N-R⁵]

| Ex. No. | —R⁵ | Physical properties |
|---|---|---|
| 94 | —CH₂-(2-pyridyl) | M.p. 216–217° C. monohydrochloride |
| 95 | —CH₂-(3-pyridyl) | M.p. >225° C. (decomp.) monohydrochloride |
| 96 | —CH₂-(4-pyridyl) | M.p. >140° C. (decomp.) monohydrochloride |
| 97 | —(CH₂)₂N(CH₃)₂ | M.p. >105° C. (decomp.) monohydrochloride |

TABLE 24

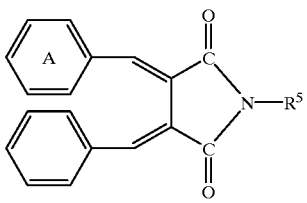

| Ex. No. | Ring A | —R⁵ | Physical properties |
|---|---|---|---|
| 98 | 2-CH₃O, 4-cyclopentyloxy-phenyl | —H | M.p. 88° C. |
| 99 | 2-CH₃O, 4-cyclopentyloxy-phenyl (isomer) | —H | M.p. 85° C. |
| 100 | 2-CH₃O, 4-cyclopentyloxy-phenyl | —CH₃ | M.p. 94–97° C. |
| 101 | 3-CH₃O, 4-CH₃O-phenyl | —H | M.p. 162–163° C. |
| 102 | 3,5-di-CH₃O-phenyl | —H | M.p. 167–169° C. |
| 103 | 3,5-di-CH₃O-phenyl | —NH₂ | M.p. 119–120° C. |

EXAMPLES 104–107

The corresponding starting compounds are treated in the same manner as in Example 23-(1), and the products thus obtained are purified by silica gel column chromatography to separate (1E,3E)-isomers from the mixture, which are further treated in the same manner as in Example 2 to give the compounds as listed in Table 25.

EXAMPLE 108

The corresponding starting compounds are treated in the same manner as in Example 23-(1) and -(2) to give the compound as listed in Table 25.

TABLE 25

[Structure: 3-cyclopentyloxy-4-methoxyphenyl with CH₃, C(=O)OCH₃, phenyl, and C(=O)NHR groups]

| Ex. No. | —R | Physical properties |
|---|---|---|
| 104 | —CH₂-(2-pyridyl) | M.p. 120–121° C. monohydrochloride |
| 105 | —CH₂-(3-pyridyl) | M.p. 149–150° C. monohydrochloride |
| 106 | —CH₂-(4-pyridyl) | M.p. 162–163° C. monohydrochloride |
| 107 | —N(CH₃)₂ | M.p. 88–89° C. (decomp.) monohydrochloride |
| 108 | —H | M.p. 166–167° C. |

EXAMPLES 109–111

The corresponding starting compounds are treated in the same manner as in Example 6 give the compounds as listed in Table 26.

EXAMPLE 112

The corresponding starting compounds are treated in the same manner as in Example 5 to give the compound as listed in Table 26.

TABLE 26

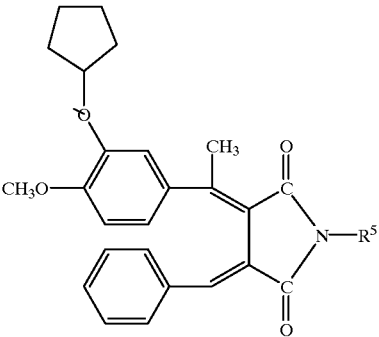

| Ex. No. | —R⁵ | Physical properties |
|---|---|---|
| 109 | 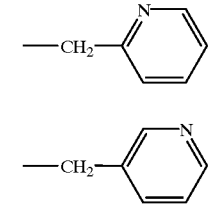 —CH₂— | monohydrochloride |
| 110 | —CH₂— 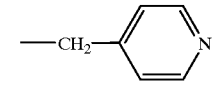 | M.p. 116–117° C. (decomp.) monohydrochloride |
| 111 | —CH₂— 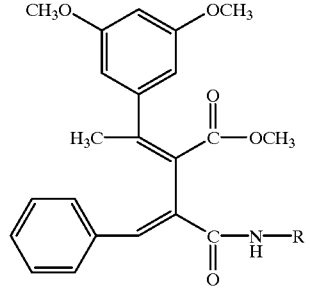 | M.p. 118–119° C. (decomp.) monohydrochloride |
| 112 | —H | M.p. 74–75° C. (decomp.) |

EXAMPLES 113–116

The corresponding starting compounds are treated in the same manner as in Example 11 to give the compounds as listed in Table 27.

TABLE 27

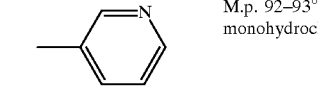

| Ex. No. | —R | Physical properties |
|---|---|---|
| 113 | 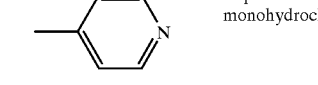 | |
| 114 | 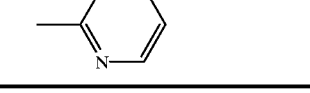 | M.p. 92–93° C. monohydrochloride |
| 115 | | M.p. 95–96° C. monohydrochloride |
| 116 | | |

EXAMPLES 117–130

The corresponding starting compounds are treated in the same manner as in Example 1-(1)→(6) to give the compounds as listed in Tables 28–29.

TABLE 28
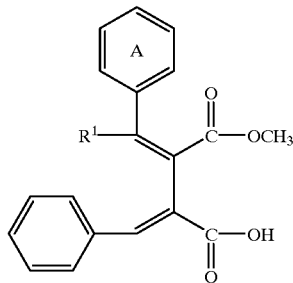
| Ex. No. | Ring A | —R¹ | Physical properties |
|---|---|---|---|
| 117 | (2-cyclopentyloxy-1-methoxy-4-yl phenyl) | —H | Not isolated. |
| 118 | (2-cyclopentyloxy-1-methoxy-4-yl phenyl) | —CH₃ | Not isolated. |
| 119 | (2-methoxy-1-cyclopentyloxy-4-yl phenyl) | —H | IR: 2958, 1712, 1690, 1605, 1509, 1269, 1034, 786, 694 cm$^{-1}$ |
| 120 | (2-methoxy-1-cyclopentyloxy-4-yl phenyl) | —CH₃ | IR: 3410, 2952, 1706, 1685, 1600, 1510, 1246, 1130, 1047, 788, 695 cm$^{-1}$ |
| 121 | (3,5-dimethoxyphenyl) | —CH₃ | IR: 2944, 1715, 1691, 1560, 1044, 789, 694 cm$^{-1}$ |
| 122 | (3,4,5-trimethoxyphenyl) | —CH₃ | IR: 2948, 1710, 1690, 1509, 1040, 694 cm$^{-1}$ |

TABLE 28-continued
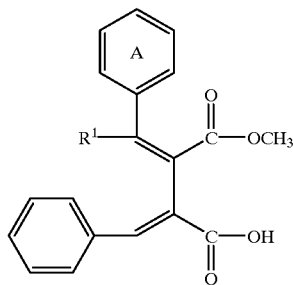
| Ex. No. | Ring A | —R¹ | Physical properties |
|---|---|---|---|
| 123 | (3,4-dimethoxy-5-chlorophenyl) | —CH₃ | IR: 2943, 1709, 1692, 1563, 1491, 1325, 1252, 1049, 1001, 853, 789, 694 cm⁻¹ |
TABLE 29
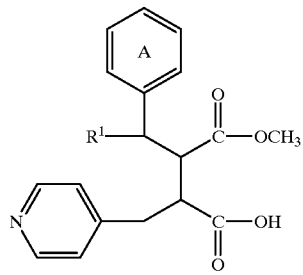
| Ex. No. | Ring A | —R¹ | Physical properties |
|---|---|---|---|
| 124 | (2-cyclopentyloxy-4-methoxyphenyl) | —H | M.p. 140–144° C. monohydrochloride |
| 125 | (2-cyclopentyloxy-4-methoxyphenyl) | —CH₃ | M.p. 171–175° C. |
| 126 | (2-methoxy-4-cyclopentyloxyphenyl) | —H | IR: 3427, 2949, 1726, 1596, 1511, 1431, 1274, 1155, 1036, 785, 605 cm⁻¹ |

TABLE 29-continued

[Structure: Ring A attached to CH(R¹)-CH(C(O)OCH₃)-CH(CH₂-4-pyridyl)-C(O)OH]

| Ex. No. | Ring A | —R¹ | Physical properties |
|---|---|---|---|
| 127 | 4-(cyclopentyloxy)-3-methoxyphenyl | —CH₃ | IR: 2944, 1695, 1603 1511, 1433, 1248, 1140, 784, 611 cm$^{-1}$ |
| 128 | 3,5-dimethoxyphenyl | —CH₃ | M.p. 172–174° C. |
| 129 | 3,4,5-trimethoxyphenyl | —CH₃ | IR: 2946, 1705, 1600, 1512, 1270, 1150, 603 cm$^{-1}$ |
| 130 | 3-chloro-4,5-dimethoxy-...phenyl | —CH₃ | Not isolated. |

EXAMPLES 131–144

The corresponding starting compounds are treated in the same manner as in Example 1-(1), -(2), -(5) and -(6), or Example 23 to give the compounds as listed in Tables 30–31.

TABLE 30

[Structure: Ring A-C(R¹)=C(COOCH₃)-C(COOH)=CH-pyridin-4-yl]

| Ex. No. | Ring A | —R¹ |
|---|---|---|
| 131 | 4-(cyclopentyloxy)-3-methoxyphenyl | —H |
| 132 | 4-(cyclopentyloxy)-3-methoxyphenyl | —CH₃ |
| 133 | 3-methoxy-4-(cyclopentyloxy)phenyl | —H |
| 134 | 3-methoxy-4-(cyclopentyloxy)phenyl | —CH₃ |

TABLE 30-continued

| Ex. No. | Ring A | —R¹ |
|---|---|---|
| 135 | 3,5-dimethoxyphenyl | —CH₃ |
| 136 | 3,4,5-trimethoxyphenyl | —CH₃ |
| 137 | 3-chloro-4,5-dimethoxy-...phenyl | —CH₃ |

TABLE 31

[Structure: Ring A-C(R¹)=C(COOCH₃)-C(COOH)=CH-pyridin-3-yl]

| Ex. No. | Ring A | —R¹ | Physical properties |
|---|---|---|---|
| 138 | 4-(cyclopentyloxy)-3-methoxyphenyl | —H | |

TABLE 31-continued

| Ex. No. | Ring A | —R¹ | Physical properties |
|---|---|---|---|
| 139 | 4-(cyclopentyloxy)-3-methoxyphenyl | —CH₃ | |
| 140 | 3-(cyclopentyloxy)-4-methoxyphenyl | —H | |
| 141 | 3-(cyclopentyloxy)-4-methoxyphenyl | —CH₃ | |
| 142 | 3,5-dimethoxyphenyl | —CH₃ | M.p. 170–172° C. |
| 143 | 3,4,5-trimethoxyphenyl | —CH₃ | M.p. 154–160° C. |
| 144 | 4-chloro-2,3-dimethoxyphenyl | —CH₃ | |

EXAMPLE 145

(1) 3,5-Dimethoxyacetophenone (246 g) and (E)-benzylidenesuccinic acid dimethyl ester (320 g) are dissolved in tert-butyl alcohol (1300 ml), and thereto is added potassium tert-butoxide (168.6 g) at room temperature, and the mixture is stirred. The mixture is allowed to cool to room temperature, and the mixture is further stirred at the same temperature for two hours. To the reaction mixture are added water (3 L) and diisopropyl ether (700 ml), and the aqueous layer is separated. To the remaining organic layer is added water, and the aqueous layer is separated. The aqueous layers are combined, and the pH value thereof is adjusted to pH 2–3 with conc. hydrochloric acid. The resulting oily product is extracted with ethyl acetate, and the extract is dried, and concentrated to give oily 1-methyl-1-(3,5- dimethoxyphenyl)-2-methoxycarbonyl-3-carboxy-4-phenylbutadiene (580 g) which is a mixture of (1Z,3E)-isomer and (1E,3E)-isomer. The oily product thus obtained is dissolved in diisopropyl ether-hexane, and the mixture is stirred at room temperature, and the precipitated crystals are collected. To the crystals is added ethyl acetate (1 L), and the mixture is heated at about 80° C., and the remaining crystals are collected by filtration to give (1E,3E)-1-methyl-1-(3,5-dimethoxyphenyl)-2-methoxycarbonyl-3-carboxy-4-phenylbutadiene (the same compound as the compound of Example 135) (117 g). The mother liquor (the filtrate) is concentrated, and ethyl acetate (700 ml) is added to the residue, and the (1Z,3E)-isomer is inoculated thereto. The mixture is stirred, and the precipitated crystals are collected to give (1Z,3E)-1-methyl-1-(3,5-dimethoxyphenyl)-2-methoxycarbonyl-3-carboxy-4-phenylbutadiene (the same compound as the compound of Example 121) (192 g).

(2) (1Z,3E)-1-Methyl-1-(3,5-dimethoxyphenyl)-2-methoxycarbonyl-3-carboxy-4-phenylbutadiene (487 g) is dissolved in methylene chloride (1000 ml), and thereto is added N,N-dimethylformamide (1 ml). To the mixture is added dropwise oxazolyl chloride (133.3 ml), and the mixture is stirred for one hour. The reaction mixture is concentrated, and the residue is dissolved in tetrahydrofuran (4 L), and thereto is added dropwise a mixture of triethylamine (214 ml) and 1-amino-4-methylpiperazine (168 mg) at 0° C. The reaction mixture is extracted with ethyl acetate, and the extract is dried, concentrated, and the residue is crystallized from diisopropyl ether to give (1Z,3E)-1-methyl-1-(3,5-dimethoxyphenyl)-2-methoxycarbonyl-3-[N-(4-methylpiperazin-1-yl)aminocarbonyl]-4-phenylbutadiene (490 g).

Yield: 81%

M.p. 117–121° C.

(3) The above product (268 g) is dissolved in chloroform, and thereto is added a 4N hydrochloric acid in ethyl acetate (125 ml) at 0° C. The mixture is poured into chilled diethyl ether, and the precipitated crystals are collected by filtration to give (1Z,3E)-1-methyl-1-(3,5-dimethoxyphenyl)-2-methoxycarbonyl-3-[N-(4-methylpiperazin-1-yl)aminocarbonyl]-4-phenylbutadiene.monohydrochloride (the same compound as the compound of Example 147) (278 g).

Yield: 97%

M.p. >234° C. (decomposed)

EXAMPLE 146

(1E,3E)-1-Methyl-1-(3,5-dimethoxyphenyl)-2-methoxycarbonyl-3-carboxy-4-phenylbutadiene (114 g) obtained in Example 145-(1) is suspended in tert-butyl alcohol, and thereto is added potassium tert-butoxide (40.1 g), and the mixture is stirred. The reaction mixture is allowed to cool to room temperature, and further stirred for two hours. The reaction mixture is treated in the same manner as in Example 145 to give (1E,3E)-1-methyl-1-(3,5-dimethoxyphenyl)-2-methoxycarbonyl-3-carboxy-4-phenylbutadiene (the same compound as the compound of Example 135) (32 g) and (1Z,3E)-1-methyl-1-(3,5-dimethoxyphenyl)-2-methoxycarbonyl-3-carboxy-4-phenylbutadiene (the same compound as the compound of Example 121) (61.5 g).

EXAMPLES 147–174

The corresponding starting compounds are treated in the same manner as in Example 11 to give the compounds as listed in Tables 32–36.

TABLE 32

| Ex. No. | —R | —R' | Physical properties |
|---|---|---|---|
| 147 | —CH$_3$ | —N(piperazine)N—CH$_3$ | M.p. >234° C. (decomp.) monohydrochloride |
| 148 | —CH$_3$ | —N(piperazine)N→O | M.p. >200° C. (decomp.) |
| 149 | —CH$_3$ | pyridyl-OCH$_3$ | M.p. >87° C. (decomp.) monohydrochloride |

TABLE 32-continued

[Structure: 3,5-dimethoxyphenyl substituted diene with H3C, COOR, phenyl, CONHR' groups]

| Ex. No. | —R | —R' | Physical properties |
|---|---|---|---|
| 150 | —CH₃ | 3-(dimethylamino)phenyl-methyl [—C₆H₄-N(CH₃)₂] | M.p. >97° C. (decomp.) monohydrochloride |
| 151 | —CH₃ | (3-methyl-5-methylisoxazol-4-yl) | M.p. 143–146° C. |
| 152 | —CH₃ | 4-(dimethylamino)phenyl-methyl [—C₆H₄-N(CH₃)₂] | M.p. >218° C. (decomp.) monohydrochloride |
| 153 | —CH₃ | (1-methylpiperidin-4-yl) | M.p. >184° C. (decomp.) monohydrochloride |

TABLE 33

[Structure: 3,5-dimethoxyphenyl substituted diene with H3C, COOR, phenyl, CONHR' groups]

| Ex. No. | —R | —R' | Physical properties |
|---|---|---|---|
| 154 | —CH₃ | 4-(morpholin-4-yl)phenyl-methyl | M.p. >215° C. (decomp.) monohydrochloride |
| 155 | —CH₃ | (pyridin-3-yl N-oxide)methyl —CH₂— | M.p. 119–120° C. |
| 156 | —CH₃ | 4-[(4-methylpiperazin-1-yl)carbonyl]phenyl-methyl | M.p. >130° C. (decomp.) monohydrochloride |

TABLE 33-continued
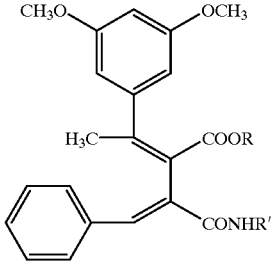
| Ex. No. | —R | —R' | Physical properties |
|---|---|---|---|
| 157 | —C$_2$H$_5$ | 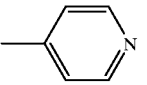 | M.p. >100° C. (decomp.) monohydrochloride |
| 158 | —C$_2$H$_5$ | 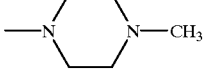 | M.p. >225° C. (decomp.) monohydrochloride |
TABLE 34
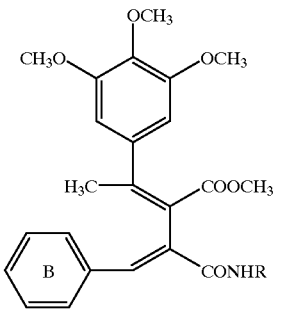
| Ex. No. | Ring B | —R | Physical properties |
|---|---|---|---|
| 159 | 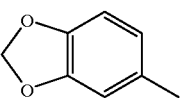 | H | M.p. 113–115° C. monohydrochloride |
| 160 | 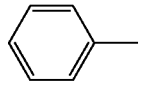 | 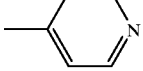 | M.p. 89–91° C. monohydrochloride |
| 161 | 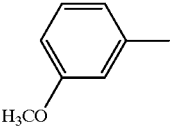 | 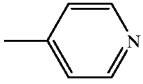 | M.p. 74–76° C. monohydrochloride |
| 162 | 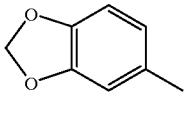 | 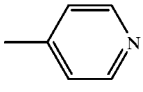 | M.p. 145–149° C. monohydrochloride |
| 163 | 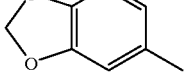 | 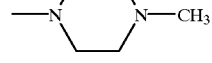 | M.p. 135–140° C. monohydrochloride |

TABLE 34-continued
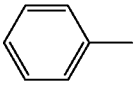
| Ex. No. | Ring B | —R | Physical properties |
|---|---|---|---|
| 164 | 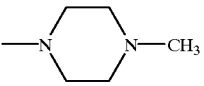 | 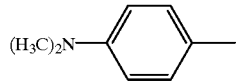 | M.p. >256° C. monohydrochloride |
TABLE 35
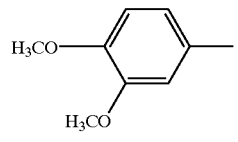
| Ex. No. | Ring B | —R | Physical properties |
|---|---|---|---|
| 165 | 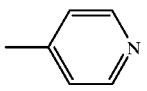 (H₃C)₂N— | H | M.p. 114–120° C. monohydrochloride |
| 166 | 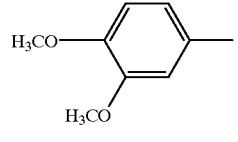 H₃CO, H₃CO |  pyridyl | M.p. 124–127° C. monohydrochloride |
| 167 | H₃CO, H₃CO | —N(piperazine)N—CH₃ | M.p. 120–127° C. monohydrochloride |

TABLE 36

| Ex. No. | Ring B | —R | Physical properties |
|---|---|---|---|
| 168 | 3-methoxyphenyl | 4-pyridyl | M.p. 91–93° C. monohydrochloride |
| 169 | 3,4-methylenedioxyphenyl | 4-pyridyl | M.p. 110–114° C. monohydrochloride |
| 170 | 3,4-dimethoxyphenyl | 4-pyridyl | M.p. 106–112° C. monohydrochloride |
| 171 | 3,4-methylenedioxyphenyl | 4-methylpiperazin-1-yl | M.p. 66–70° C. monohydrochloride |
| 172 | 3,4-dimethoxyphenyl | 4-methylpiperazin-1-yl | M.p. 60–65° C. monohydrochloride |
| 173 | 3,5-dimethoxyphenyl | 4-methylpiperazin-1-yl | M.p. >124° C. (decomp.) monohydrochloride |
| 174 | 3,5-dimethoxyphenyl | 4-methylpiperazin-1-yl | M.p. >130° C. (decomp.) monohydrochloride |

EXAMPLES 175–179

The corresponding starting compounds are treated in the same manner as in Example 49 to give the compounds as listed in Table 37.

TABLE 37

[Structure: 1,3-butadiene with CH3O/OCH3 substituted phenyl on C4, H3C and Ring B on C1, COOCH3 on C3, CONHR on C2]

| Ex. No. | Ring B | —R | Physical properties |
|---|---|---|---|
| 175 | 4-pyridyl N-oxide | H | M.p. 201–202° C. |
| 176 | 3-pyridyl | H | M.p. 196–198° C. (decomp.) monohydrochloride |
| 177 | 4-pyridyl | —CH₃ | M.p. 105–109° C. monohydrochloride |
| 178 | 4-pyridyl N-oxide | —CH₃ | M.p. 159–160° C. |
| 179 | 3-pyridyl N-oxide | —CH₃ | M.p. 160–161° C. |

EXAMPLE 180

(1) Potassium tert-butoxide (14.2 g) is dissolved in tert-butyl alcohol (120 ml), and thereto is added dropwise a solution of 3,5-dimethoxybenzaldehyde (20 g) and dimethyl succinate (21.1 g) in tetrahydrofuran. The mixture is stirred at room temperature for 30 minutes, and water and isopropyl ether are added to the mixture. The aqueous layer is separated, and the remaining organic layer is further extracted with water. The aqueous layers are combined, and the pH value thereof is adjusted to pH 2–3 with conc. hydrochloric acid. The resulting oily product is extracted with ethyl acetate, and the extract is dried, concentrated under reduced pressure to give 4-(3,5-dimethoxyphenyl)-3-carboxy-3-butenoic acid methyl ester (42 g) as an oily product.

(2) The above product is dissolved in methanol (200 ml), and thereto is added conc. sulfuric acid (2 ml), and the mixture is refluxed for 13 hours. The reaction mixture is concentrated, and thereto are added water and diethyl ether. The organic layer is collected, washed, dried and concentrated under reduced pressure. The resulting residue is purified by silica gel column chromatography (eluent; ethyl acetate:hexane=1:4) to give (E)-2-(3,5-dimethoxybenzylidene)succinic acid dimethyl ester (18.4 g).

Yield: 52%

(3) The above product (18.4 g) and 3,5-dimethoxyacetophenone (11.83 g) are dissolved in tert-butyl alcohol (70 ml), and thereto is added potassium tert-butoxide (8.42 g), and the mixture is stirred. The reaction mixture is stirred at room temperature for two hours, and thereto are added water and isopropyl ether. The aqueous layer is separated, and the remaining organic layer is extracted with water. The aqueous layers are combined, and the pH value thereof is adjusted to pH 2–3 with conc. hydrochloric acid. The resulting oily product is extracted with ethyl acetate, and the extract is dried, and concentrated under reduced pressure. Isopropyl ether is added to the residue, and the precipitated crystals are collected by filtration to give (1Z,3E)-1-methyl-1-(3,5-dimethoxyphenyl)-2-methoxycarbonyl-3-carboxy-4-(3,5-dimethoxyphenyl)butadiene (4.74 g).

Yield: 17.1%

(4) The mother liquor (the filtrate) is concentrated, and isopropyl ether is added to the residue. The mixture is stirred at room temperature, and the precipitated crystals are collected to give 1-methyl-1-(3,5-dimethoxyphenyl)-2-methoxycarbonyl-3-carboxy-4-(3,5-dimethoxyphenyl)butadiene (9.2 g) in the form of a mixture of (1Z,3E)-isomer and (1E,3E)-isomer thereof.

Yield: 33.3%

(5) The above mixture (9.0 g) is suspended in tert-butyl alcohol (50 ml), and thereto is added potassium tert-butoxide (2.51 g). The mixture is stirred at room temperature for two hours, and then acidified by adding thereto water and 12N hydrochloric acid. The mixture is extracted with ethyl acetate, and the extract is dried, concentrated. To the residue is added diisopropyl ether (30 ml), and the mixture is stirred at 0° C. The precipitated crystals are collected to give (1Z,3E)- 1-methyl-1-(3,5-dimethoxyphenyl)-2-methoxycarbonyl-3-carboxy-4-(3,5-dimethoxyphenyl)butadiene (3.6 g).

Yield: 13.0%

M.p. 137–140° C.

IR: 1724, 1670, 1591, 1423, 1206, 1156 cm$^{-1}$ (6) (1Z,3E)-1-Methyl-1-(3,5-dimethoxyphenyl)-2-methoxycarbonyl-3-carboxy-4-(3,5-dimethoxyphenyl)butadiene (1.70 g) is dissolved in dichloromethane (20 ml), and thereto are added a catalytic amount of N,N-dimethylformamide and oxalyl chloride (0.4 ml). The mixture is stirred at room temperature for one hour, and the reaction mixture is concentrated. To the residue is added tetrahydrofuran (20 ml), and the mixture is added dropwise into a solution of 1-methylpiperazine (462 mg) and triethylamine (0.65 ml) in tetrahydrofuran (20 ml), and the mixture is stirred at 0° C. for 30 minutes. To the reaction mixture are added water and ethyl acetate, and the organic layer is collected. The remaining aqueous layer is extracted with ethyl acetate. The organic layers are combined, dried, and concentrated. The residue is purified by silica gel column chromatography (eluent; chloroform:methanol=30:1) to give (1Z,3E)-1-methyl-1-(3,5-dimethoxyphenyl)-2-methoxycarbonyl-3-(4-methylpiperazin-1-yl)carbonyl-4-(3,5-dimethoxyphenyl)butadiene (2.0 g).

Yield: 99.2%

IR: 1727,1591, 1425, 1200, 1155 cm$^{-1}$ (7) The above product (2.0 g) is dissolved in chloroform (10 ml), and thereto is added 4N hydrochloric acid in ethyl acetate (1.05 ml) at 0° C., and the mixture is stirred for several minutes. To the reaction mixture is added dimethyl ether, and the mixture is stirred. The precipitated crystals are collected by filtration to give (1Z,3E)-1-methyl-1-(3,5-dimethoxyphenyl)-2-methoxycarbonyl-3-(4- methylpiperazin-1-yl)carbonyl-4-(3,5-dimethoxyphenyl) butadiene.monohydrochloride (1.70 g). The structure and the physical properties thereof are shown in Table 38.

Yield: 79.5%
M.p. >133° C. (decomposed)
IR: 3436, 1725, 1591, 1425, 1206, 1156 cm$^{-1}$

EXAMPLES 181–183

The corresponding starting compounds are treated in the same manner as in Example 180 to give the compounds as listed in Table 38.

TABLE 38

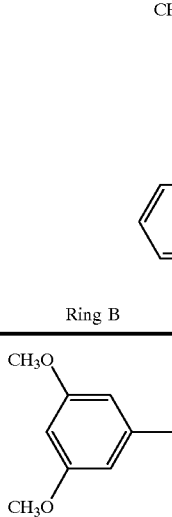

| Ex. No. | Ring B | —R | Physical properties |
|---|---|---|---|
| 180 | 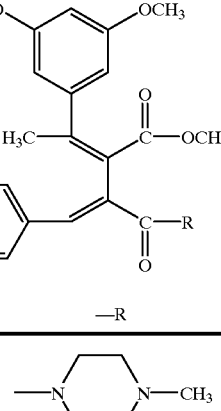 | 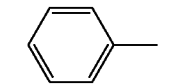 | M.p. >133° C. (decomp.) monohydrochloride |
| 181 | 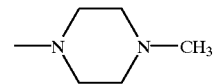 | 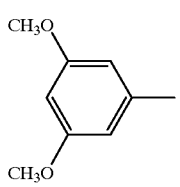 | M.p. 130° C. monohydrochloride |
| 182 | 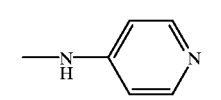 | 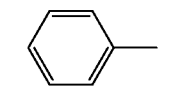 | M.p. 202–204° C. monohydrochloride |
| 183 | 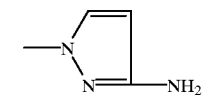 | | M.p.<110° C. |

EXAMPLE 184

The corresponding starting compounds are treated in the same manner as in Example 26 to give the compound as listed in Table 39.

TABLE 39
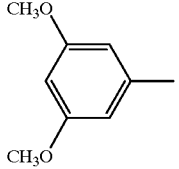
| Ex. No. | Ring A | —R | Physical properties |
|---|---|---|---|
| 184 | 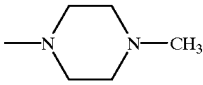 |  | M.p. 212–214° C. monohydrochloride |
EXAMPLES 185–189
The corresponding starting compounds are treated in the same manner as in Example 11 to give the compounds as listed in Table 40.
TABLE 40
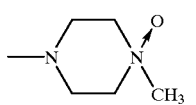
| Ex. No. | —R | —R' | Physical properties |
|---|---|---|---|
| 185 | —CH$_3$ | 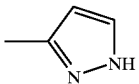 | M.p. >184° C. (decomp.) monohydrochloride |
| 186 | —CH$_3$ | 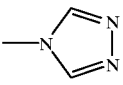 | M.p. 65° C. (decomp.) |
| 187 | —CH$_3$ | | M.p. <70° C. monohydrochloride |
| 188 | —CH$_3$ | | M.p. 130–132° C. monohydrochloride |

TABLE 40-continued

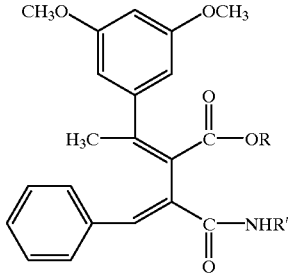

| Ex. No. | —R | —R' | Physical properties |
|---|---|---|---|
| 189 | —CH$_3$ | 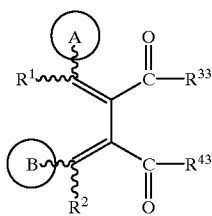 | M.p. <50° C. |

INDUSTRIAL APPLICATION

The butadiene derivative (1-a), the amidobutadiene derivative (1-b) and the pyrrolidine derivative (2) of the present invention and a pharmaceutically acceptable salt thereof show an excellent PAI-1 inhibitory activity, and hence, they are useful in the prophylaxis or treatment of various thrombus such as myocardial infarction, intra-atrial thrombus in atrial fibrillation, arterial sclerosis, angina pectoris, stroke, pulmonary infarction, deep venous thrombus (DVT), disseminated intravascular coagulation syndrome (DIC), diabetic complications, restenosis after percutaneous transluminal coronary angioplasty (PTCA), etc.

Besides, the present compounds (1-a), (1-b) and (2) also show excellent bioavailability, safety as a medicament, and stability, and hence, they show low toxicity and high safety as a medicament. Especially, among the present compounds (1-b), the compounds having a trans(E)-configuration based on the double bond binding to Ring B, a cis(Z)-configuration based on the double bond binding to Ring A show (i) high solubility in water, (ii) high stability to the metabolism in the liver, (iii) low toxicity against in the liver and chromosome, (iv) high stability against light.

What is claimed is:

1. An amidobutadiene compound of the formula (1-b):

(1-b)

wherein
Ring A is a substituted or unsubstituted heterocyclic group, or a benzene ring which may optionally be substituted by one to three groups selected from a C$_{1-6}$ alkyl group, a C$_{1-20}$ alkoxy group, a C$_{3-10}$ cycloalkyloxy group, a nitro group, a hydroxy group, a substituted or unsubstituted amino group and a halogen atom,
Ring B is a substituted or unsubstituted heterocyclic group, or a benzene ring which may optionally be substituted by one to three groups selected from a C$_{1-6}$ alkoxy group, a C$_{1-4}$ alkylenedioxy group and a di-C$_{1-6}$ alkylamino group,
the configuration based on the double bond binding to Ring B is trans(E)-configuration, and the configuration based on the double bond binding to Ring A is cis(Z)-configuration,
either one of R$^1$ and R$^2$ is a C$_{1-6}$ alkyl group, and the other is a hydrogen atom or a C$_{1-6}$ alkyl group,
one of a group: —COR$^{33}$ and a group: —COR$^{43}$ is an amidated carboxyl group, and the other is a carboxyl group which may optionally be esterified, provided that (a) both Ring A and Ring B are not simultaneously an unsubstituted benzene ring, and (b) when Ring A is a tri-C$_{1-6}$ alkoxybenzene ring, then Ring B is a substituted or unsubstituted heterocyclic group, or at least one of R$^1$ and R$^2$ is a C$_{1-6}$ alkyl group, or a pharmaceutically acceptable salt thereof.

2. A compound according to claim 1, wherein a group: —COR$^{33}$ is an esterified carboxyl group, and a group: —COR$^{43}$ is an amidated carboxyl group, or a pharmaceutically acceptable salt thereof.

3. A compound according to any one of claims 1 and 2, wherein a group: —COR$^{43}$ is a carbamoyl group which may optionally be substituted by 1 or 2 groups selected from a substituted or unsubstituted C$_{1-20}$ alkyl group, a substituted or unsubstituted phenyl group, a substituted or unsubstituted amino group and a substituted or unsubstituted nitrogen-containing heterocyclic group, or a pharmaceutically acceptable salt thereof.

4. A compound according to any one of claims 1 and 2, wherein Ring A is a benzene ring substituted by one to three groups selected from a C$_{1-20}$ alkoxy group, a C$_{3-10}$ cycloalkyloxy group, a nitro group, a hydroxy group, a di-C$_{1-6}$ alkylamino group and a halogen atom, Ring B is a nitrogen-containing heteromonocyclic group, a benzene ring or a C$_{1-4}$ alkylenedioxy-substituted benzene ring, or a pharmaceutically acceptable salt thereof.

5. A compound according to any one of claims 1 and 2, wherein Ring A is a benzene ring substituted by two or three groups selected from a C$_{1-6}$ alkoxy group a C$_{3-10}$ cycloalkyloxy group, a nitro group, a hydroxy group, a di-$C_{1-6}$ alkylamino group and a halogen atom, Ring B is a pyridine ring, a benzene ring, or a $C_{1-4}$ alkylenedioxy-substituted benzene ring, $R^1$ is a $C_{1-6}$ alkyl group, $R^2$ is a hydrogen atom, a group: —$COR^{33}$ is a $C_{2-7}$ alkoxycarbonyl group or a $C_{1-6}$ alkoxy-substituted $C_{2-7}$ alkoxycarbonyl group, a group: —$COR^{43}$ is a carbamoyl group which may optionally be substituted by one group selected from a pyridyl group, an oxo-substituted pyridyl group, an amino-substituted pyridyl group, a $C_{1-6}$ alkoxy-substituted pyridyl group, a $C_{1-6}$ alkyl-substituted piperidyl group, a $C_{1-6}$ alkyl-substituted piperazinyl group, a piperazinyl group substituted by a $C_{1-6}$ alkyl group and an oxo group, a $C_{1-6}$ alkyl-substituted isoxazolyl group, a pyrazolyl group, a triazolyl group, a pyridyl-substituted $C_{1-6}$ alkyl group, an oxo-substituted pyridyl-$C_{1-6}$ alkyl group, a di-$C_{1-6}$ alkylphenyl group, a morpholinophenyl group, a $C_{1-6}$ alkylpiperazinylcarbonylphenyl group, a hydroxy-$C_{1-6}$ alkyl group and a di-$C_{1-6}$ alkylamino group, or a group of the formula:

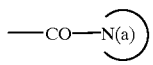

in which Ring (a) is a substituted or unsubstituted 5- or 6-membered nitrogen-containing heteromonocyclic group, or a pharmaceutically acceptable salt thereof.

6. A compound according to any one of claims 1 and 2, wherein Ring A is a benzene ring substituted by two or three groups selected from a methoxy group, a cyclopentyloxy group, a nitro group, a hydroxy group, a dimethylamino group and a chlorine atom, $R^1$ is a methyl group, a group: —$COR^{33}$ is a methoxycarbonyl group, an isopropyloxycarbonyl group or a 2-methoxyethoxycarbonyl group, a group: —$COR^{43}$ is a carbamoyl group optionally substituted by one group selected from a pyridylmethyl group, a 2-aminopyridyl group, a pyridyl group, a 1-oxopyridyl group, a 4-methylpiperazinyl group, a 4-methyl-4-oxopiperazinyl group, a 1-methylpiperidyl group, a 5-methylisoxazolyl group, a 3-pyrazolyl group, a 1,3,4-triazolyl group, a 1-oxopyridylmethyl group, a dimethylaminoethyl group, a hydroxyethyl group and a dimethylamino group, or a pharmaceutically acceptable salt thereof.

7. A compound according to claim 1, which is a member selected from (1Z,3E)-1-methyl-1-(3,5-dimethoxyphenyl)-2-methoxycarbonyl-3-[N-(4-methylpiperazin-1-yl)aminocarbonyl]-4-phenylbutadiene, (1Z,3E)-1-methyl-1-(3,5-dimethoxyphenyl)-2-methoxycarbonyl-3-[N-(4-pyridyl)aminocarbonyl]-4-(3,4-methylenedioxyphenyl)butadiene, (1Z,3E)-1-methyl-1-(3,5-dimethoxyphenyl)-2-methoxycarbonyl-3-[N-(4-pyridylmethyl)aminocarbonyl]-4-phenylbutadiene, (1Z,3E)-1-methyl-1-(3-chloro-4,5-dimethoxyphenyl)-2-methoxycarbonyl-3-[N-(3-pyridylmethyl)aminocarbonyl]-4-phenylbutadiene, and (1Z,3E)-1-methyl-1-(3-chloro-4,5-dimethoxyphenyl)-2-methoxycarbonyl-3-aminocarbonyl-4-(4-pyridyl)butadiene, or a pharmaceutically acceptable salt thereof.

8. (1Z,3E)-1-Methyl-1-(3,5-dimethoxyphenyl)-2-methoxycarbonyl-3-[N-(4-methylpiperazin-1-yl)aminocarbonyl]-4-phenylbutadiene, or a pharmaceutically acceptable salt thereof.

9. (1Z,3E)-1-Methyl-1-(3,5-dimethoxyphenyl)-2-methoxycarbonyl-3-[N-(4-pyridyl)aminocarbonyl]-4-(3,4-methylenedioxyphenyl)butadiene, or a pharmaceutically acceptable salt thereof.

10. A process for preparing an amidobutadiene compound of the formula (1-b):

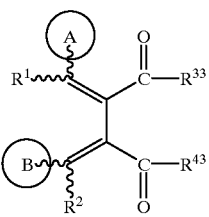

(1-b)

wherein
Ring A is a substituted or unsubstituted heterocyclic group, or a benzene ring which may optionally be substituted by one to three groups selected from a $C_{1-6}$ alkyl group, a $C_{1-20}$ alkoxy group, a $C_{3-10}$ cycloalkyloxy group, a nitro group, a hydroxy group, a substituted or unsubstituted amino group and a halogen atom, Ring B is a substituted or unsubstituted heterocyclic group, or a benzene ring which may optionally be substituted by one to three groups selected from a $C_{1-6}$ alkoxy group, a $C_{1-4}$ alkylenedioxy group and a di-$C_{1-6}$ alkylamino group, the configuration based on the double bond binding to Ring B is trans(E)-configuration, and the configuration based on the double bond binding to Ring A is cis(Z)-configuration, either one of $R^1$ and $R^2$ is a $C_{1-6}$ alkyl group, and the other is a hydrogen atom or a $C_{1-6}$ alkyl group, one of a group: —$COR^{33}$ and a group: —$COR^{43}$ is an amidated carboxyl group, and the other is a carboxyl group which may optionally be esterified, provided that (a) both Ring A and Ring B are not simultaneously an unsubstituted benzene ring, and (b) when Ring A is a tri-$C_{1-6}$ alkoxybenzene ring, then Ring B is a substituted or unsubstituted heterocyclic group, or at least one of $R^1$ and $R^2$ is a $C_{1-6}$ alkyl group, or a pharmaceutically acceptable salt thereof, which comprises reacting a butadiene compound of the formula (1-a):

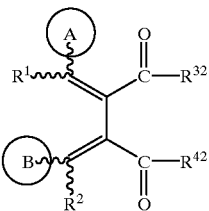

(1-a)

wherein Ring A, Ring B, the configuration based on the double bond binding to Ring B, the configuration based on the double bond binding to Ring A, $R^1$ and $R^2$ are the same as defined above, one of a group: —$COR^{32}$ and a group: —$COR^{42}$ is a carboxyl group, and the other is a carboxyl group which is esterified, or a salt thereof, or a reactive derivative thereof, with a compound of the formula (5):

(5)

wherein $R^{40}$ is a substituted or unsubstituted amino group, if necessary, followed by converting the product into a pharmaceutically acceptable salt thereof.

11. A pharmaceutical composition which comprises a therapeutically effective amount of a compound or a pharmaceutically acceptable salt thereof as set forth in claim 8 and a pharmaceutically acceptable carrier or diluent thereto.

12. A method for treatment and/or prophylaxis of thrombus in mammal, which comprises administering to the mammal a therapeutically effective amount of a compound or a pharmaceutically acceptable salt thereof as set forth in claim 8.

13. A method for treatment and/or prophylaxis of restenosis after percutaneous transluminal coronary angioplasty in mammal, which comprises administering to the mammal a therapeutically effective amount of a compound or a pharmaceutically acceptable salt thereof as set forth in claim 8.

14. A method for treatment and/or prophylaxis of deep venous thrombus in mammal, which comprises administering to the mammal a therapeutically effective amount of a compound or a pharmaceutically acceptable salt thereof as set forth in claim 8.

15. A pharmaceutical composition which comprises a therapeutically effective amount of a compound or a pharmaceutically acceptable salt thereof as set forth in claim 1 and a pharmaceutically acceptable carrier or diluent thereto.

16. A method for treatment and/or prophylaxis of thrombus in mammal, which comprises administering to the mammal a therapeutically effective amount of a compound or a pharmaceutically acceptable salt thereof as set forth in claim 1.

17. A method for treatment and/or prophylaxis of restenosis after percutaneous transluminal coronary angioplasty in mammal, which comprises administering to the mammal a therapeutically effective amount of a compound or a pharmaceutically acceptable salt thereof as set forth in claim 1.

18. A method for treatment and/or prophylaxis of deep venous thrombus in mammal, which comprises administering to the mammal a therapeutically effective amount of a compound or a pharmaceutically acceptable salt thereof as set forth in claim 1.

19. An amidobutadiene compound of the formula:

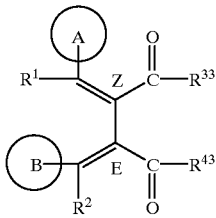

wherein

Ring A is a benzene ring substituted by two or three groups selected from a $C_{1-20}$ alkoxy group, a $C_{3-10}$ cycloalkoxy group, a hydroxy group, and a halogen atom, Ring B is a pyridine ring, a benzene ring, or a $C_{1-4}$ alkylenedioxy-substituted benzene ring, the configuration based on the double bond binding to Ring B is trans(E)-configuration, and the configuration based on the double bond binding to Ring A is cis (Z)-configuration, $R^1$ is a $C_{1-6}$ alkyl group, $R^2$ is a hydrogen atom, a group: —$COR^{33}$ is a $C_{2-7}$ alkoxycarbonyl group, a group: —$COR^{43}$ is a carbamoyl group which may optionally be substituted by one group selected from a pyridyl group, an oxo-substituted pyridyl group, an amino-substituted pyridyl group, a $C_{1-6}$ alkoxy-substituted pyridyl group, a $C_{1-6}$ alkyl-substituted piperidyl group, a $C_{1-6}$ alkyl-substituted piperazinyl group, a piperazinyl group substituted by a $C_{1-6}$ alkyl group and an oxo group, a pyridyl-substituted $C_{1-6}$ alkyl group, and an oxo-substituted pyridyl-$C_{1-6}$ alkyl group, or a pharmaceutically acceptable salt thereof.

20. An amidobutadiene compound of the formula:

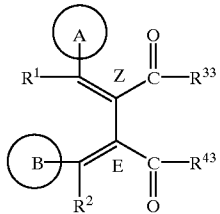

wherein

Ring A is a benzene ring substituted by two or three groups selected from a $C_{1-20}$ alkoxy group, Ring B is a benzene ring, or a $C_{1-4}$ alkylenedioxy-substituted benzene ring, the configuration based on the double bond binding to Ring B is trans(E)-configuration, and the configuration based on the double bond binding to Ring A is cis(Z)-configuration, $R^1$ is a $C_{1-6}$ alkyl group, $R^2$ is a hydrogen atom, a group: —$COR^{33}$ is a $C_{2-7}$ alkoxycarbonyl group, a group: —$COR^{43}$ is a carbamoyl group which may optionally be substituted by one group selected from a pyridyl group, an oxo-substituted pyridyl group, a $C_{1-6}$ alkyl-substituted piperazinyl group, a pyridyl-substituted $C_{1-6}$ alkyl group, and an oxo-substituted pyridyl-$C_{1-6}$ alkyl group, or a pharmaceutically acceptable salt thereof.

* * * * *

UNITED STATES PATENT AND TRADEMARK OFFICE
CERTIFICATE OF CORRECTION

PATENT NO.    : 6,248,743 B1                                                Page 1 of 1
DATED         : June 19, 2001
INVENTOR(S)   : Hiroshi Ohmizu et al.

It is certified that error appears in the above-identified patent and that said Letters Patent is hereby corrected as shown below:

<u>Column 74,</u>
Line 67, after "$C_{1-6}$ alkoxy group", insert -- , -- (a comma).

Signed and Sealed this

Fourth Day of June, 2002

*Attest:*

*Attesting Officer*

JAMES E. ROGAN
*Director of the United States Patent and Trademark Office*